(12) United States Patent
Bhattacharya et al.

(10) Patent No.: US 8,420,080 B2
(45) Date of Patent: Apr. 16, 2013

(54) METHODS FOR TREATING ADULT RESPIRATORY DISTRESS SYNDROME

(75) Inventors: Jahar Bhattacharya, New York City, NY (US); Sadiqa K. Quadri, Teaneck, NJ (US); Shonit Das, Bronx, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 229 days.

(21) Appl. No.: 12/681,058

(22) PCT Filed: Oct. 1, 2008

(86) PCT No.: PCT/US2008/078483
§ 371 (c)(1),
(2), (4) Date: Mar. 31, 2010

(87) PCT Pub. No.: WO2009/046129
PCT Pub. Date: Apr. 9, 2009

(65) Prior Publication Data
US 2012/0027742 A1 Feb. 2, 2012

Related U.S. Application Data

(60) Provisional application No. 60/976,779, filed on Oct. 1, 2007.

(51) Int. Cl.
*A61K 38/46* (2006.01)
(52) U.S. Cl.
USPC ..................................................... 424/94.65
(58) Field of Classification Search ............... 424/94.65
See application file for complete search history.

(56) References Cited

U.S. PATENT DOCUMENTS

| | | | |
|---|---|---|---|
| 8,003,613 B2 * | 8/2011 | Cance et al. ................ | 514/18.9 |
| 2002/0061599 A1 | 5/2002 | Elling et al. | |
| 2007/0134257 A1 | 6/2007 | Mascarenhas | |

FOREIGN PATENT DOCUMENTS

WO WO 2004/027018 A2 4/2004

OTHER PUBLICATIONS

Cashman et al. 2003; Evidence of protein transduction but not intracellular transport by proteins fused to HIV Tat in retinal cell culcture and in vivo. Molecular Therapy 8(1): 130-142.*
Pons et al. 2004; Enterophilin-1 interacts with focal adhesion kinase and decreases 1 integrins in intestinal Caco-2 cells. J. Biol. Chem. 279(10): 9270-9277.*
Piantadosi et al. 2004; The acute respiratory distress syndrome. Ann Intern Med 141:460-470.*
Cao, G. et al., In Vivo Delivery of a Bcl-xL Fusion Protein Containing the TAT Protein Transduction Domain Protects against Ischemic Brain Injury and Neuronal Apoptosis, journal, The Journal of Neuroscience, Apr. 2002, pp. 5423-5431, vol. 22, No. 13, Society for Neuroscience, US.
Garcia, J. et al., Sphingosine 1-phosphate promotes endothelial cell barrier integrity by Edg-dependent cytoskeletal rearrangement, journal, The Journal of Clinical Investigation, Jul. 2001, pp. 689-701, vol. 108, No. 5.
Holinstat, M. et al., Suppression of RhoA Activity by Focal Adhesion Kinase-induced Activation of p190RhoGAP, journal, Journal of Biological Chemistry, Nov. 2005, pp. 2296-2305, vol. 281, No. 4.
International Search Report and Written Opinion, PCT/US2008/078483, Mar. 12, 2009, pp. 1-12.
Mehta, D. et al., Modulatory role of focal adhesion kinase in regulating human pulmonary arterial endothelial barrier function, jounral, Journal of Physiology, Dec. 2001, pp. 779-789, vol. 539, No. 3, The Physiological Society, United States.
Mehta, D. et al., Signaling Mechanisms Regulating Endthelial Permeability, journal, 2006, pp. 279-367, vol. 86, The American Physiological Society.
Morris, M. C. et al., A peptide carrier for the delivery of biologically active proteins into mammalian cells, journal, Oct. 2001, pp. 1173-1176, vol. 19, Nature Publishing Group.
Quadri, S. et al., Resealing of endothelial junctions by focal adhesion kinase, journal, Sep. 2006, pp. L334-L342, vol. 292, The American Physiological Society.
Quadri, S. K. et al., Endothelial Barrier Strengthening by Activation of Focal Adhesion Kinase, journal, The Journal of Biological Chemistry, Jan. 2003, pp. 13342-13349, vol. 278, No. 15, The American Society for Biochemistry and Molecular Biology, Inc., United States.
Rubenfeld, G. et al., Incidence and Outcomes of Acute Lung Injury, journal, The New England Journal of Medicine, 2005, pp. 1685-1693, Massachusetts Medical Society, United States.
Safdar, Z. et al., Hyperosmolarity enhances the lung capillary barrier, journal, The Journal of Clinical Investigation, Sep. 2003, pp. 1541-1549, vol. 112, No. 10.
Safdar, Z. et al., Inhibition of Acid-induced Lung Inquiry by Hyperosmolar Sucrose in Rats, journal, American Journal of Respiratory and Critical Care Medicine, Jul. 2005, pp. 1002-1007, vol. 172.
Schober, M. et al., Focal adhesion kinase modulates tension signaling to control actin and focal adhesion dynamics, journal, JCB: Article, Feb. 2007, pp. 667-680, vol. 176, No. 5, The Rockefeller University Press.
Usatyuk, P. et al, Regulation of reactive oxygen species-induced endothelial cell-cell and cell-matrix contacts by focal adhesion kinase and adherens junction proteins, journal, Jul. 2005, pp. L999-L1010, vol. 289, The American Physiological Society.
Wu, M. et al., Focal adhesion kinase mediates porcine venular hyperpermeability elicited by vascular endothelial growth factor, journal, J Physiol, Aug. 2003, pp. 691-699, The Physiological Society, United States.

* cited by examiner

*Primary Examiner* — Karen Cochrane Carlson
(74) *Attorney, Agent, or Firm* — Evans & Molinelli PLLC; Judith A. Evans

(57) ABSTRACT

We have discovered that the activated phosphorylated form of focal adhesion kinase (hereafter "FAKp") strengthens the microvascular endothelial cell (EC) junctions that form a barrier in pulmonary endothelia, and the increased barrier helps to prevent acute lung injury (ALI) and acute respiratory distress syndrome (ARDS). Thus certain embodiments of the invention are directed to prevention and treatment of ALI and ARDS by administering a therapeutically effective amount of FAKp to subjects at risk of developing or diagnosed as having either ALI or ARDS.

8 Claims, 17 Drawing Sheets

E-cad + WT    + WT+FAKp each pair: mean±se, n=3, *p<.05

METHODS FOR TREATING ADULT RESPIRATORY DISTRESS SYNDROME

CROSS-REFERENCE TO RELATED APPLICATIONS

This present application is a national phase application of PCT Application No. PCT/US2008/078483, filed on Oct. 1, 2008 and claims priority of U.S. Provisional Application. 60/976,779, filed Oct. 1, 2007, the entire contents of which are hereby incorporated by reference as if fully set forth herein, under 35 U.S.C. §119(e).

STATEMENT OF GOVERNMENTAL INTEREST

This invention was made with government support under Grant No. HL36024 awarded by The National Institutes of Health. The government has certain rights in the invention.

BACKGROUND OF THE INVENTION

1. Field of the Invention

Methods for treating and preventing acute respiratory distress syndrome.

2. Description of the Related Art

Adult Respiratory Distress Syndrome (ARDS) is a descriptive expression which is applied to a large number of acute, diffusely infiltrative pulmonary lesions of different etiology if they are associated with a severe gas exchange disorder (in particular arterial hypoxemia). The acute respiratory distress syndrome (ARDS; also known as the adult respiratory distress syndrome) is an inflammatory disorder characterized by the accumulation of neutrophils in the lung and the development of non-cardiogenic pulmonary edema [Repine, Lancet (1992); 339: 466-469]. ARDS is part of a spectrum of acute lung inflammatory diseases involving adults and neonates. In neonates, the disease is often called hyaline membrane disease. Once established, ARDS has an approximately 50% mortality, largely because there are still no specific treatments for the syndrome. Patients with major trauma, sepsis or other specific disorders are at risk for ARDS.

Acute respiratory distress syndrome (ARDS) is characterized by the development of sudden breathlessness within hours to days of an inciting event. ARDS typically develops within 12-48 hours after the inciting event, although, in rare instances, it may take up to a few days. Persons developing ARDS are critically ill, often with multisystem organ failure. It is a life-threatening condition; therefore, hospitalization is required for prompt management.

ARDS is associated with severe and diffuse injury to the alveolar-capillary membrane (the air sacs and small blood vessels) of the lungs. Fluid accumulates in some alveoli of the lungs, while some other alveoli collapse. This alveolar damage impedes the exchange of oxygen and carbon dioxide, which leads to a reduced concentration of oxygen in the blood. Low levels of oxygen in the blood cause damage to other vital organs of the body such as the kidneys.

ARDS occurs in children as well as adults. The estimated annual frequency of ARDS is reported as 75 cases per 100,000 people. Mortality (death) rates have been reported to be in the range of 30-40%.

A number of risk factors are associated with the development of ARDS, including sepsis (presence of various pathogenic microorganisms, or their toxins, in the blood or tissues), severe traumatic injury (especially multiple fractures), severe head injury, injury to the chest, aspiration, diffuse pulmonary infection, near-drowning, fracture of the long bones, acute pancreatitis, drug overdose, aspiration, viral pneumonias, bacterial and fungal pneumonias, near drowning, toxic inhalations, transfusion, and cardiopulmonary bypass surgery. Among these causes, sepsis has a particularly high incidence and poor prognosis for acute lung injury (Montgomery, A. B. et al., Am. Rev. Respir. Dis. (1985) 132, 485-489, Knaus, W. A. et al., Am. J. Respir. Crit. Care Med. (1994) 150, 311-317; and Bernard, G. R. et al., Am. J. Respir. Crit. Care Med. (1994) 149, 818-824). The definition of sepsis syndrome specifies that it does not necessarily require clinical findings as an infection (Bone, R. C. et al., Chest (1992) 101, 1644-1655: Crit. Care Med. (1992) 20, 864-874). Sepsis as used herein collectively refers to both sepsis and sepsis syndrome.

Persons with ARDS are hospitalized and require treatment in an intensive care unit. Treatment is primarily supportive using a mechanical respirator and supplemental oxygen. Intravenous fluids are given to provide nutrition and prevent dehydration, and are carefully monitored to prevent fluid from accumulating in the lungs (pulmonary edema). Because infection is often the underlying cause of ARDS, appropriate antibiotic therapy is administered. Corticosteroids may sometimes be administered in late phases of ARDS to reduce inflammation or if the patient is in shock. Diuretics to eliminate fluid from the lungs are also used Inhaled drugs administered by respiratory therapists are often administered to decrease inflammation and provide respiratory comfort. While there is a 60-70% survival rate, many survivors of ARDS have residual lung impairment. Typically, the lung dysfunction is mild, but ARDS can lead to severe lung damage and a reduced health-related quality of life.

As was mentioned above, the therapy of ARDS consists mainly in the earliest possible application of different forms of ventilation to raise the oxygen concentration of the respiratory air. However, ventilation with pressure and high $FiO_2$ (Fraction of Inspired Oxygen; proportion of oxygen in the respiratory air), can damage the lungs therefore necessitating even higher pressures and higher $FiO_2$ in order to obtain an adequate oxygenation of the blood.

Pathological conditions associated with ARDS include pulmonary edema due to increased permeability based on injuries in the pulmonary microvascular endothelia (Matthay, M. A., Clin. Chest Med. (1990) 11, 575-580). A variety of pharmacological agents including pulmonary vasodilators, anti-inflammatory agents, anti-oxidants, inhibitors of thromboxane synthetase, exogenous surfactants, inhaled vasodilators (nitric oxide), anti-endotoxin and anti-cytokine agents (Kollef et al., supra and Ware et al et al., supra) have been tried without success. Therefore there is a need for new therapies to prevent or treat ARDS or other forms of acute lung injury (ALI).

SUMMARY OF THE INVENTION

Certain aspects of the invention are directed to a molecule in which a protein or peptide intended for intracellular delivery, preferably human activated focal adhesion kinase (FAKp) or a biologically active fragment, derivative or variant thereof, is noncovalently bound to a transport protein. The protein or peptide in the molecule has a histidine tag, the transport protein is chelated to a metal ion selected from the group comprising copper, nickel, zinc and cobalt, and the metal atom is noncovalently bound to the histidine tag on the protein/peptide. Any transport protein can be used, including Chariot©, pepetratin, TAT fragment, a signal sequence-based peptide, and transportan.

Another aspect of the invention is directed to a method for treating or preventing ALI and ARDS, by administering a therapeutically effective amount of activated focal adhesion kinase (FAKp) or a biologically active fragment, derivative or variant thereof, preferably human recombinant FAKp. In a preferred embodiment FAKp is administered by inhalation or intravenous injection. In another aspect this method further includes administering a therapeutically effective amount of high osmolar sucrose, administered either together with FAKp or on the same day.

Other aspects of the invention are directed to pharmaceutical compositions, such as a pharmaceutical composition that includes activated focal adhesion kinase (FAKp), or a biologically active fragment, derivative or variant thereof, preferably human recombinant FAKp. In a preferred embodiment the activated focal adhesion kinase is bound to a transport protein such as Chariot©, pepetratin, TAT fragment, a signal sequence-based peptide, and transportan. In a preferred embodiment of the pharmaceutical composition, activated focal adhesion kinase has a histidine tag, the transport protein is chelated to a metal ion that is a member selected from the group comprising copper, nickel, zinc and cobalt, and the metal atom is noncovalently bound to the histidine tag.

In another aspect FAKp is administered therapeutically to treat cancer, or other disease associated with reduced focal adhesions, such as inflammatory conditions including sepsis, arthritis, hepatitis, nephritis, hyaline membrane disease, cerebral inflammation, pulmonary or cerebral edema, and neonatal bronchopulmonary dysplasia.

A typical therapeutically effective amount of activated focal adhesion kinase is an amount of from about 0.1-20 micrograms/kilogram body weight.

Other aspects are drawn to a kit that has a transport protein, one end of which is chelated to a metal ion that is a member selected from the group comprising copper, nickel, zinc and cobalt. Another kit has this transport protein plus a cargo protein intended for delivery to a target cell, one end of which comprises a histidine tag and the other end of which is optionally chelated to a metal ion including copper, nickel, zinc and cobalt.

BRIEF DESCRIPTION OF THE DRAWINGS

The present invention is illustrated by way of example, and not by way of limitation, in the figures of the accompanying drawings and in which.

FAKp loading decreased Sp to 0.2±0.2 (P<0.05; n=3), indicating EC barrier enhancement.

Figure 17:
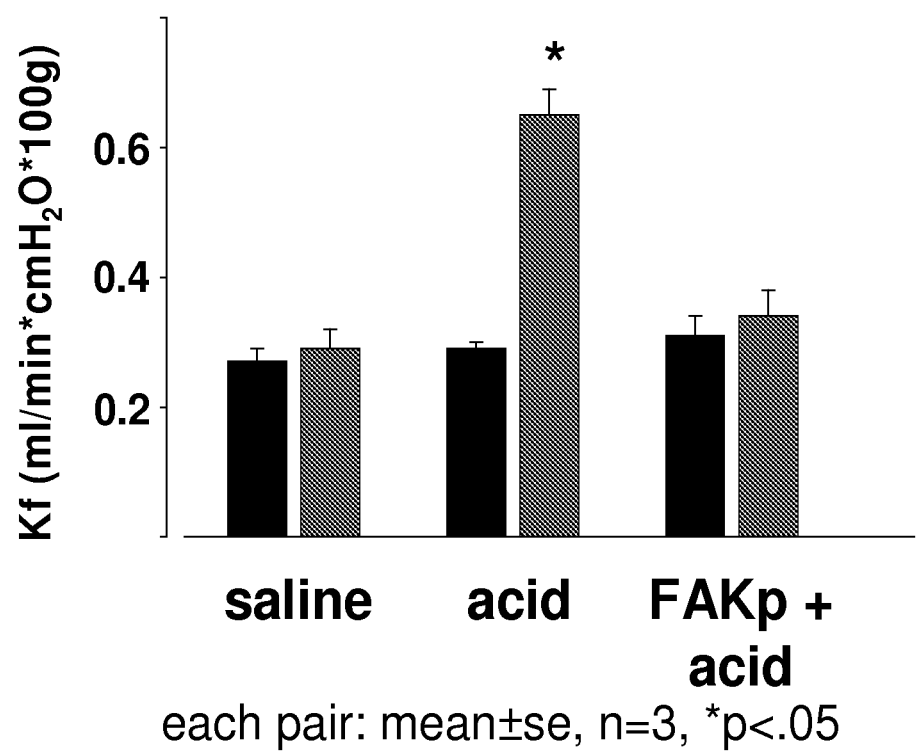

FIG. 17. Effect of FAKp on Lung microvascular filtration coefficient (Kf). To determine global permeability responses, Kf was measured after intra-tracheal acid instillation (2 ml/kg, HCl pH 1.5) in the anesthetized mouse. After 2 h of acid instillation, Kf was markedly elevated above control (saline instillation) However, tail vein injections of FAKp given 1 h prior to acid instillation completely abrogated the Kf increase.

Figure 18:
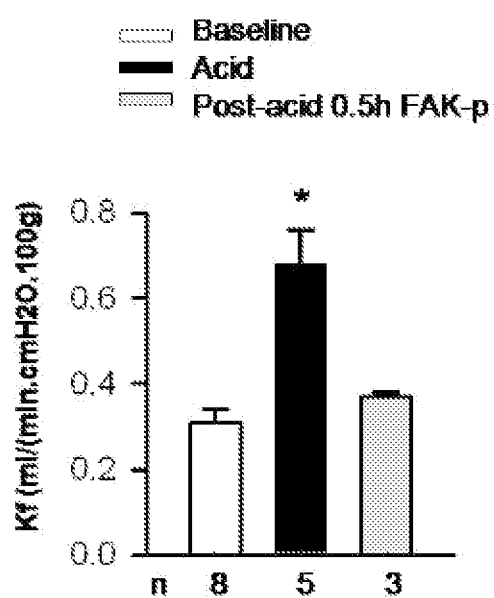

FIG. 18. Lung microvascular barrier protection in isolated blood-perfused mouse lungs by post-treatment with FAKp. N, number of experiments. Kf, lung microvascular filtration coefficient, *P<0.05 compared with baseline. In the protected group, FAKp was given by the intravascular route 30 after intra-tracheal acid instillation.

Figure 19:
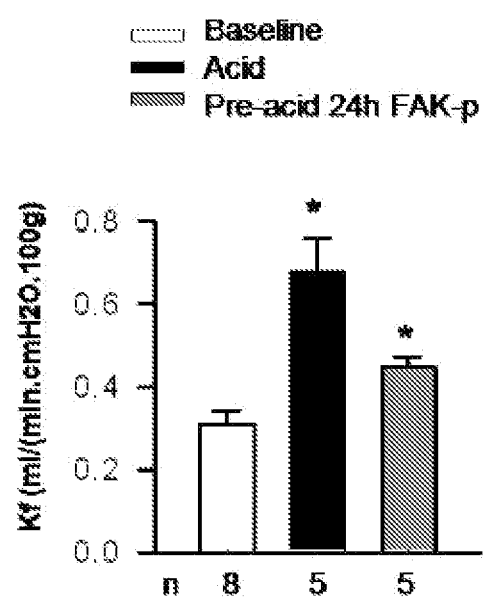

FIG. 19. Lung microvascular barrier protection in isolated blood-perfused mouse lungs by pre-treatment with FAKp. N, number of experiments. Kf, lung microvascular filtration coefficient, *P<0.05 compared with baseline. In the protected group, FAKp was given by the intravascular route 24 hours prior to intra-tracheal acid instillation.

Figure 20:
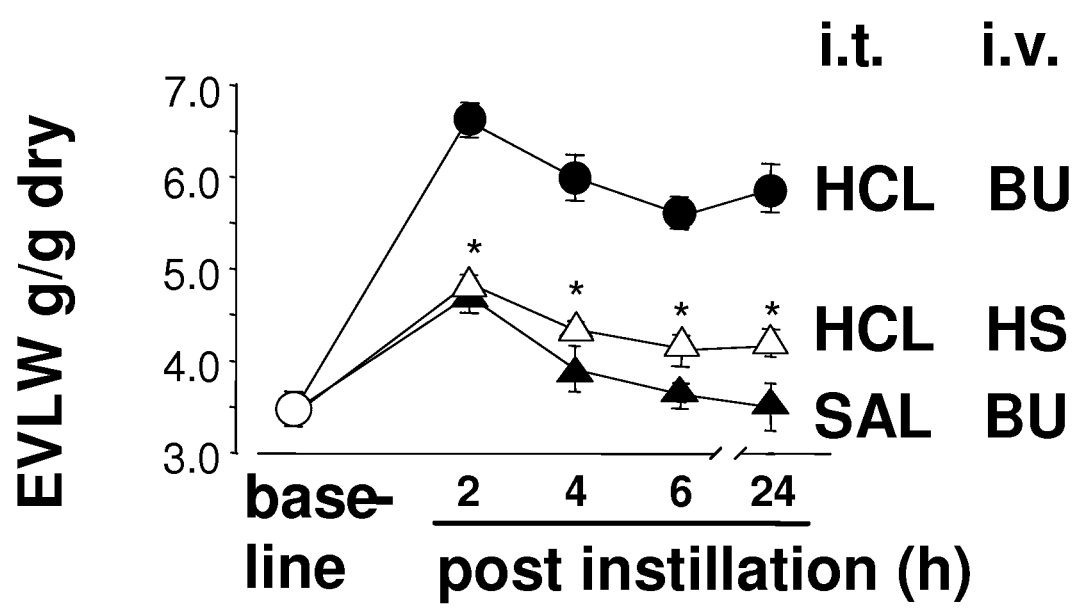

FIG. 20. Effect of hyperosmolar sucrose on extravascular lung water (EVLW). To determine protection in the long term, we gave intra-tracheal (IT) acid (HCL) instillation (2 ml/kg, HCl pH 1.5) or saline (SAL) in the anesthetized rat followed 30 minutes later by intravenous infusion (IV) of either buffer (BU) or hyperosmolar sucrose (HS). Then after rats recovered from anesthesia, EVLW content was determined at different durations for 24 hours. N=3 for each group.

FIG. 21A. Effect of hyperosmolar sucrose (HS) on leukocyte accumulation in bronchioalveolar lavage fluid (BAL) of lipopolysaccharide (LPS) treated rats. Either LPS or saline (SAL) was administered by intra-tracheal infusion. 30 minutes later, rats were given an intravenous infusion of either hyperosmolar sucrose (HS) or buffer (BU). After 24 h, BAL samples were obtained and leukocytes counted. N=3 for each group.

FIG. 21B. Effect of hyperosmolar sucrose (HS) on protein accumulation in bronchioalveolar lavage fluid (BAL) of lipopolysaccharide (LPS) treated rats. Either LPS or saline (SAL) was administered by intra-tracheal infusion. 30 minutes later, rats were given an intravenous infusion of either hyperosmolar sucrose (HS) or buffer (BU). After 24 h, BAL samples were obtained and protein content determined. N=3 for each group.

Figure 22:
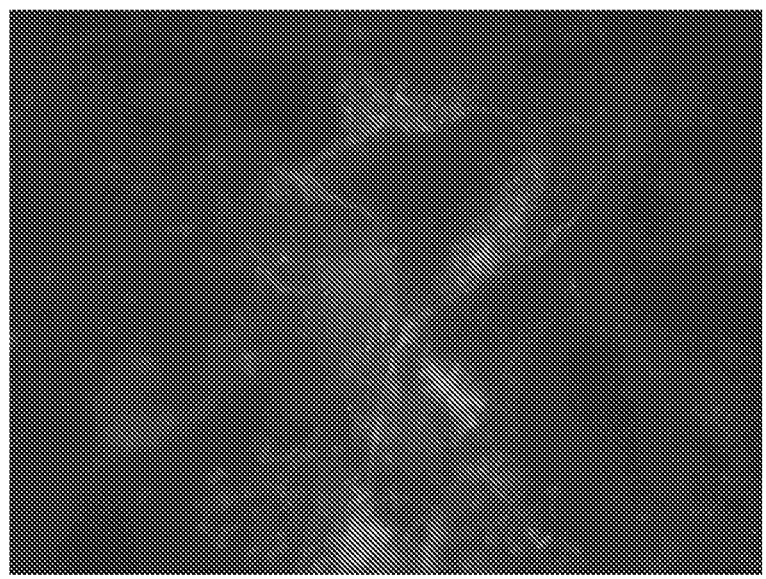

FIG. 22. TAT-FAKp uptake in cultured lung EC. TAT-FAKp was added to lung endothelial monolayers. After 30 min, image taken by conventional fluorescence microscopy shows FAKp localization at focal adhesions.

Figure 23:

FIG. 23. FAKp localization to endothelial focal adhesions. TAT-FAKp was added to lung endothelial monolayers. After 30 min, image taken by total internal reflection microscopy shows FAKp localization at focal adhesions on the abluminal membrane.

Figure 24:
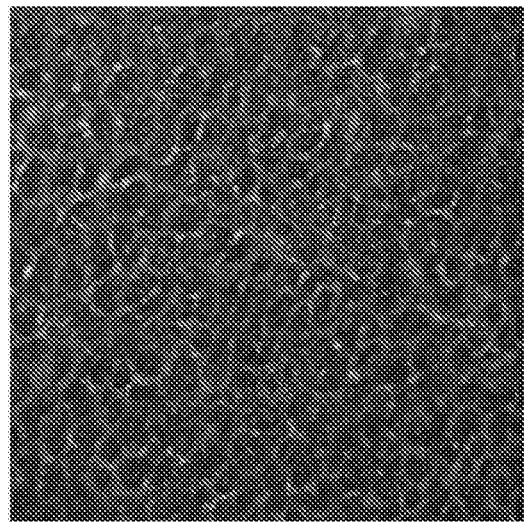
Figure 24:
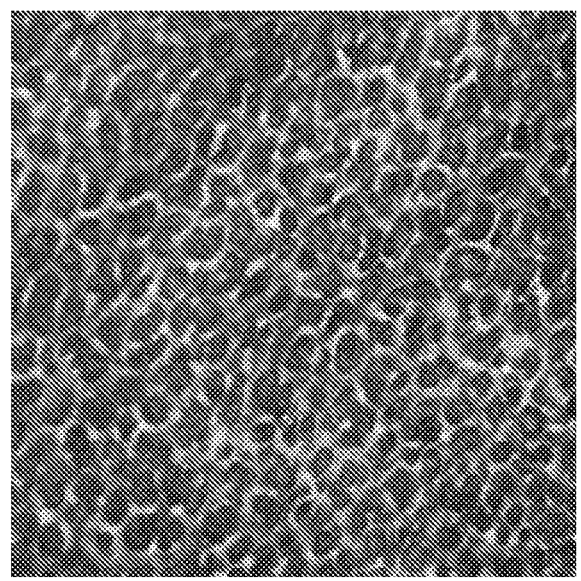

FIG. 24. FAKp uptake in isolated blood-perfused mouse lung. Low power view of lung surface shows FAKp uptake in lung microvessels before (LEFT) and 40 minutes after (RIGHT) addition of TAT-FAKp to the perfusion. Green: GFP-stained lung microvessels. Red: TAT-FAKp.

Figure 25:
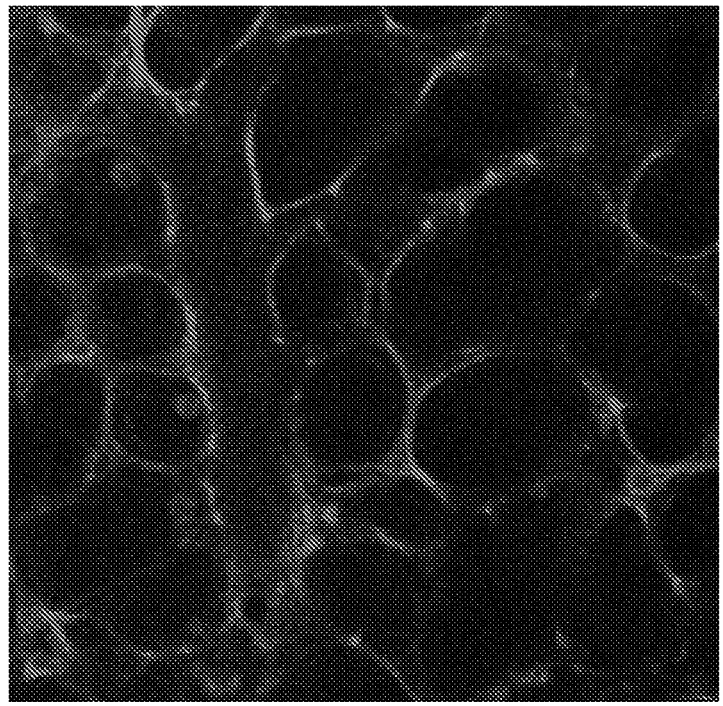

FIG. 25. FAKp uptake in isolated blood-perfused mouse lung. Procedures were same as in the previous figure. High-power view of lung surface shows FAKp uptake (red staining) in lung microvessels.

Figure 26:
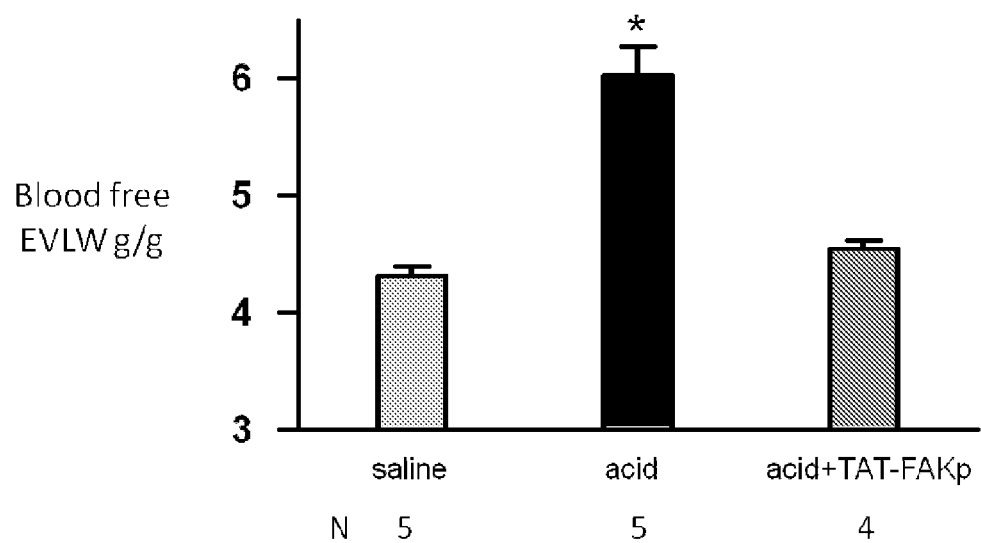

FIG. 26. Inhibition of acid-induced lung injury by TAT-FAKp. Mouse lungs were assayed for extravascular lung water (EVLW) content before (saline) or after (acid) intra-tracheal acid instillation. In the protection group (acid+TAT-FAKp), TAT-FAKp was given 30 minutes after acid instillation. *P<0.05 versus saline control. N=number of lungs.

DEFINITIONS

Focal adhesion kinase (FAK) means a 125 KDa non-receptor protein-tyrosine kinase, including any biologically active fragment, modification, derivative or variant thereof. FAK is localized at focal adhesion plaques where cells attach to the extracellular matrix. FAK possesses binding sites for a number of proteins, most importantly Src (the transforming (sarcoma inducing) gene of Rous sarcoma virus) family kinases. The gene sequence, cDNA sequence and amino acid sequence of human FAK are known. The complete cds for *Homo sapiens* focal adhesion kinase mRNA, is ACCESSION NO: L05186; VERSION L05186.1; which also provides the amino acid sequence. The cDNA for making recombinant FAKp for use in the present invention would be a histidine-tagged cDNA that encodes full-length human FAK that is constitutively phosphorylated at tyrosine 397.

Activated FAK means the phosphorylated form of FAK that is referred to herein as "FAKp", including any biologically active fragment, modification, derivative or variant thereof. FAKp includes isolated and purified FAKp obtained using any means known in the art including the method described in Example 1 by which we made, isolated and purified recombinant FAKp, and it includes chemically synthesized FAKp. For treating human subjects, recombinant, human FAKp is preferred. Isolated and purified FAKp means substantially pure FAKp and may include small amounts of impurities, as long as it yields a single band by gel electrophoresis (a standard technique for protein identification in a sample). FAK can be activated in different ways: it can be synthesized as an active form or it can be activated by Src or ATP.

Biologically active fragment means a fragment of a protein that retains the biological activity of the protein or that exhibits a similar, but not necessarily identical, activity to the protein, preferably FAK or FAKp. The biological activity of the fragment may include an improved desired activity such as enhancing barrier function, or a decreased undesirable activity.

A therapeutically effective amount of a protein or polypeptide (i.e., an effective dosage of FAKp) is an amount that achieves the desired therapeutic result. For example, a therapeutically effective amount is an amount that ameliorates one or more symptoms of the disease, including ALI or ARDS, or that decreases lung endothelial cell (EC) permeability, i.e. increases the EC barrier in an animal, preferably a human, has or is at risk of developing ALI or ARDS.

The terms "inhibit", "elevate", "increase", "decrease" or the like, e.g., which denote quantitative differences between two states, refer to a difference, e.g., a statistically significant difference, between the two states.

DETAILED DESCRIPTION

We have discovered that the activated phosphorylated form of focal adhesion kinase (hereafter "FAKp") strengthens the microvascular endothelial cell (EC) junctions that form a barrier in pulmonary endothelia, and the increased barrier helps to prevent acute lung injury (ALI) and ARDS. Thus certain embodiments of the invention are directed to prevention and treatment of ALI and ARDS by administering a therapeutically effective amount of FAKp to persons (or other mammals) at risk of developing or diagnosed as having either ALI or ARDS. We have also discovered a new method for linking FAKp (or any other protein or peptide) to a transport protein that is taken up by the target cells to facilitate targeted drug delivery.

ALI is a condition in which endothelial cell barrier deterioration causes lung microvascular hyperpermeability, leading to debilitating pulmonary edema. ALI carries high mortality and morbidity in all age groups (2). However, until now specific EC barrier therapy has not been available. ARDS includes a large number of acute, diffusely infiltrative pulmonary lesions of different etiology if they are associated with a severe gas exchange disorder (in particular arterial hypoxemia). Therefore both ALI and ARDS are associated with a degeneration of the pulmonary EC barrier.

Considerable evidence attributes microvascular hyperpermeability to receptor-mediated EC contraction. By contrast, EC barrier-enhancing mechanisms are relatively less understood. Several of our findings point to the EC barrier protective effect of hyperosmolar sucrose. These include (i) increase of electrical resistance (TER) across cultured EC monolayers (1), (ii) decrease of the capillary hydraulic conductivity (Lp) in lung microvessels in situ (5), (iii) protection against agonist-induced hyperpermeability in lung microvessels (5), and (iv) protection against ALI induced by acid instillation in whole lungs (6). Exposure to hyperosmolar sucrose is a benign treatment that increases plasma osmolarity by only ~60 milliosmoles above baseline for a brief 15 minute period resulting in EC barrier protection that lasts for about 1-2 hours. No untoward effects have been reported in anaesthetized animals (5, 6). In preliminary studies, animals remained symptom free for up to 24 hours after hyperosmolar sucrose infusion.

We have also shown that the hyperosmolar barrier enhancement is associated with increased FAK activity and increased junctional content of E-cadherin. (1, 5). If FAK activity is blocked by overexpressing the kinase-deficient FAK mutant (del-FAK), the increase in the EC barrier and E-cadherin is also blocked (1). Hyperosmolar sucrose initially causes cell shrinkage, and the resulting membrane/matrix interaction induces formation of focal adhesions in the endothelial cell membrane that activate FAK (1, 12). We now show that activated FAK (FAKp) in turn increases junctional E-cadherin, thereby increasing the EC barrier. Findings from other labs describing a role for FAK in increased EC barrier formation have been mixed. Anti-sense oligonucleotide reduction of FAK expression worsened thrombin-induced barrier deterioration heart vessels (13, 14), supporting our view that FAK positively regulates the barrier. However, findings in large vessel EC indicate a barrier deteriorating role for FAK (15, 16). It is possible that microvascular and large vessel EC may differ in barrier mechanisms (17).

We reported earlier that FAK reseals endothelial cell junctions in lung cells in vitro after exposure to hydrogen peroxide (19). We now show that administration of activated phosphorylated FAK (FAKp) reduces lung damage in mice that have been exposed to intratracheal acid instillation in vivo, and administration of FAKp before acid exposure greatly reduces post-injury ALI.

Activated FAK Reseals Endothelial Cell (EC) Junctions

Endothelial cell (EC) junctions determine vascular barrier properties and are subject to transient opening to allow liquid flux from blood to tissue. Although EC junctions open in the presence of permeability-enhancing factors such as oxidants, the mechanisms by which they reseal remain inadequately understood. To model opening and resealing of EC junctions in the presence of an oxidant, we quantified changes in hydrogen peroxide ($H_2O_2$)-induced transendothelial resistance (TER) in monolayers of rat lung microvascular EC. During a 30-minute exposure, $H_2O_2$ (100 microM) decreased TER initially for approximately the first 10 minutes of the 30 minute exposure, then it increased for the next 10 min, indicating junctional opening. Subsequently, despite continuous presence of $H_2O_2$, TER recovered to baseline, indicating the activation of junctional resealing mechanisms. These bimodal TER transients matched the time course of loss and then gain of E-cadherin at EC junctions. The timing of the TER decrease matched the onset of focal adhesion formation, while F-actin increase at the cell periphery occurred with a time course that complemented the recovery of peripheral E-cadherin. In monolayers expressing a focal adhesion kinase (FAK) mutant (del-FAK), the initial $H_2O_2$-induced junctional opening was present, but the subsequent junctional recovery was blocked. Further, expression of transfected E-cadherin was evident at the cell periphery of wild-type but not del-FAK-expressing EC. E-cadherin over expression in del-FAK-expressing EC failed to affect a major rescue of the junctional resealing response (19). These findings indicated that in oxidant-induced EC junction opening, FAK plays a critical role in remodeling the adherens junction to reseal the barrier.

The next set of experiments tested whether the lung microvascular EC barrier could be strengthened by adding activated recombinant FAK (FAKp) isolated and purified as described in Example 1, FIGS. 2-5.

Figure 1:
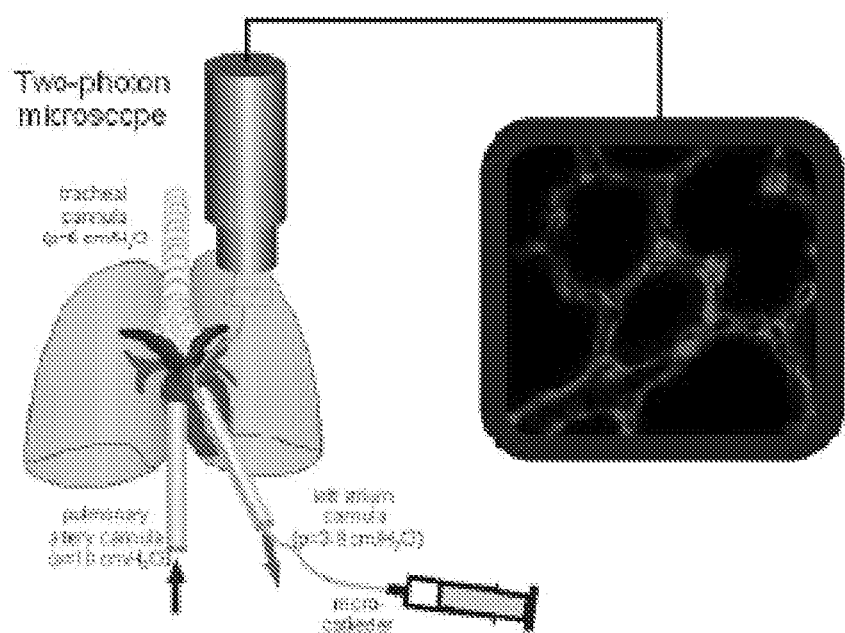
FIG. 1. Principles of optical imaging in the rodent lung. A microscope is placed over the surface of the isolated, blood-perfused rat or mouse lung. Fluorescence-emitting agents are introduced either through a catheter in the left atrial cannula, or directly in the blood stream.

To infuse FAKp to a localized area of the vasculature, a venous microcatheter (PE 10) was introduced into isolated lungs. To facilitate delivery, FAKp was conjugated to Chariot© reagent to make a Chariot©-protein product as described in Example 1. Calcein red, FITC-dextran (20 kD, 5 mg/ml, 1 ml/hr), a Chariot©-FAKp (10 µg/ml) labeled with a fluorescent label (BODIPY—dipyrromethene boron difluoride) were administered intravenously through the microcatheter at rate of 1 ml/h for 20 minutes at 37 degrees Centigrade. Intraluminal (Cv) and interstitial (Ci) fluorescence in the tissue space lying between the vessel bifurcation and an alveolar corner was continuously monitored. The lungs were held at a left atrial pressure of 8 cm $H_2O$ during the infusions and imaging. The lungs were positioned under a multi-photon imaging system (Radiance 2100 MP, Biorad) for analysis and fluorescence was excited at 800 nm by a pulsed Ti-sapphire laser (Chameleon, Coherent). Acquired images were subjected to computer-based image analysis (Metamorph, Meta Imaging Corp.) as shown in the schematic of FIG. 1 and described in Example 1.

Figure 6:
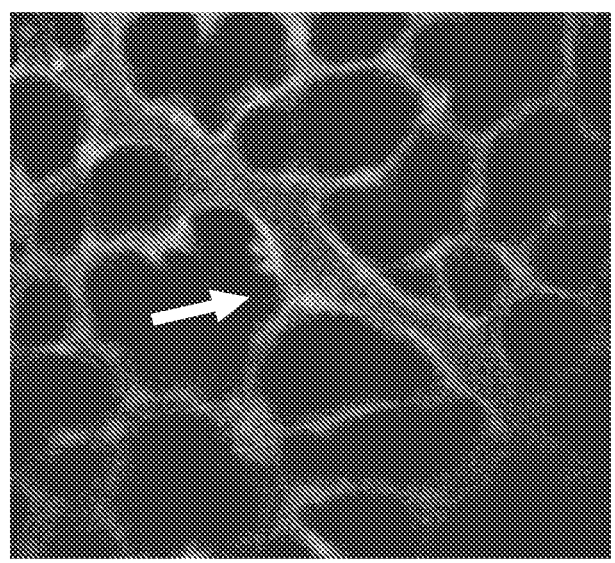
FIG. 6. Fluorescence of BODIPY-FAKp in a live capillary network. In isolated, perfused lungs, a 20 minute intravenous infusion of BODIPY-FAKp bound to the Chariot© agent revealed extensive fluorescence on the lung surface consistent with endothelial uptake (e.g. arrow).

After the 20 minute intravenous infusion of BODIPY-FAKp extensive fluorescence was seen on the lung surface (FIG. 6), which is consistent with uptake by the endothelial cells. Any cell-penetrating peptide such as Chariot© (also called protein transport peptides) that facilitates uptake of FAKp into target cells can be used in the present invention. Examples of transport proteins are described below.

Figure 7:
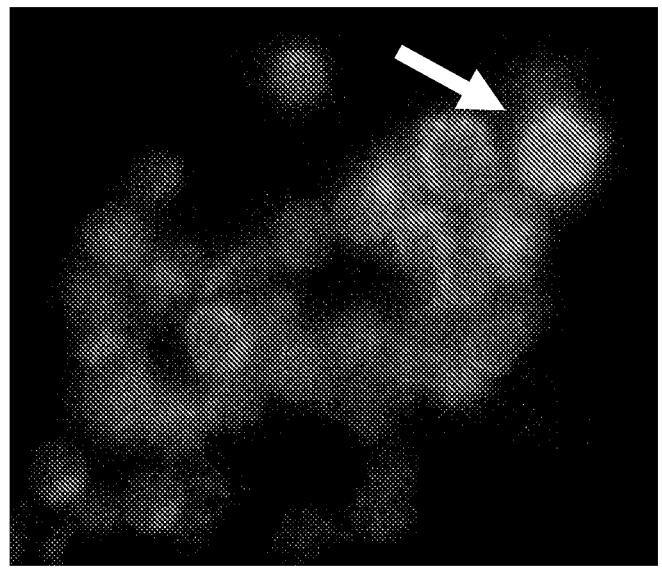
FIG. 7. Fluorescence of BODIPY-FAKp in freshly isolated endothelial cells (FLEC). FLEC obtained from an isolated-perfused lung 20 minutes after intravenous infusion of BODIPY-FAKp bound to Chariot© show dotted fluorescence of BODIPY-FAKp confirming endothelial uptake of BODIPY-FAKp.
Figure 8:
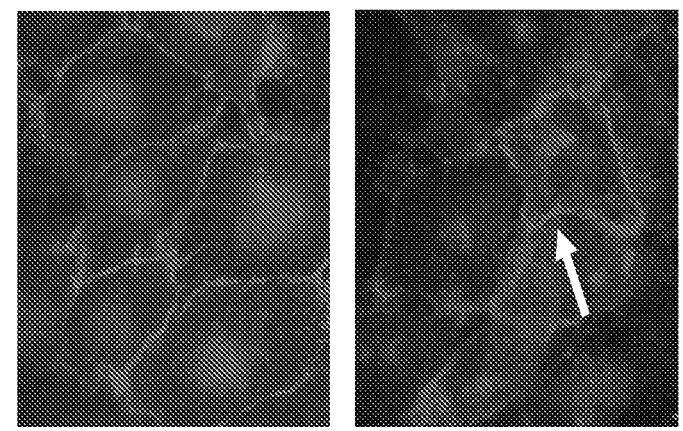
FIG. 8. E-cadherin staining in FAKp⁻loaded endothelial cells. In rat lung microvascular endothelial cell (RLMEC) monolayers, a 1 h exposure to FAKp increased E-cadherin expression (e.g. arrow) above control (WT).
Figure 9:
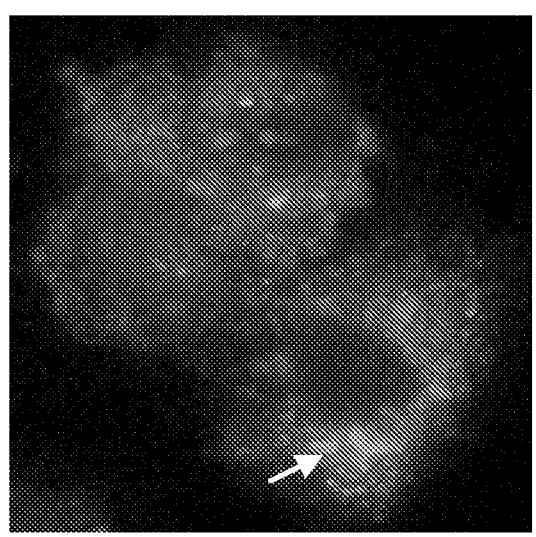
FIG. 9. BODIPY staining in FAKp⁻loaded endothelial cells. RLMEC loaded with FAKp-BODIPY show BODIPY staining confirming uptake of BODIPY-FAKp.

To study FAKp uptake by EC, fluorescently labeled FAKp (BODIPY-FAKp) was injected in the tail vein of a mouse; freshly isolated lung EC (FLEC) analyzed one hour after injection showed fluorescence in mouse lung microvascular endothelial cells. (FIG. 7). Control images were black. We further determined that FAKp increased E-cadherin expression (FIG. 8) by about 50% above control levels in rat lung microvascular endothelial cell (RLMEC) monolayers (FIG. 9).

Figure 10:
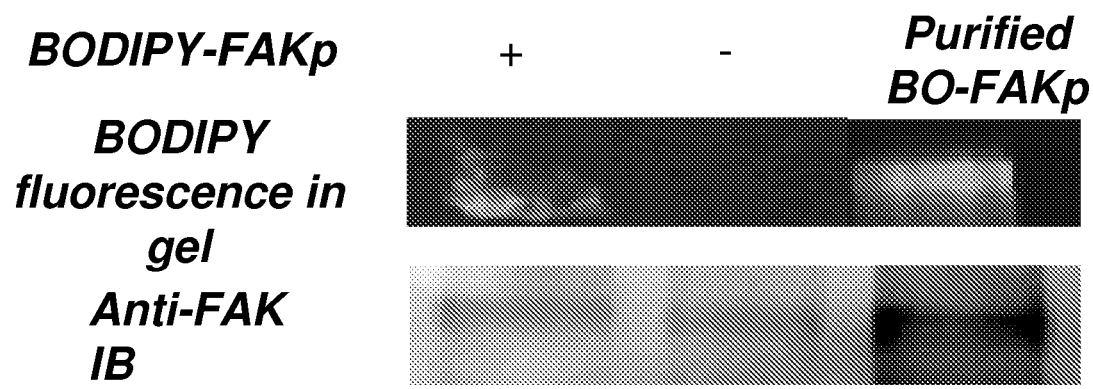
FIG. 10. Paxillin immunoprecipitation. In mouse, 1 h after tail vein infusion of FAKp-Chariot© immunoprecipitation of paxillin from lung tissue showed pulldown of FAKp (lower immunoblot) indicating that the exogenous FAKp co-associated intracellularly with paxillin. BODIPY fluorescence in immunoprecipitate (upper panel) confirmed FAKp uptake in lung tissue.
Figure 11:
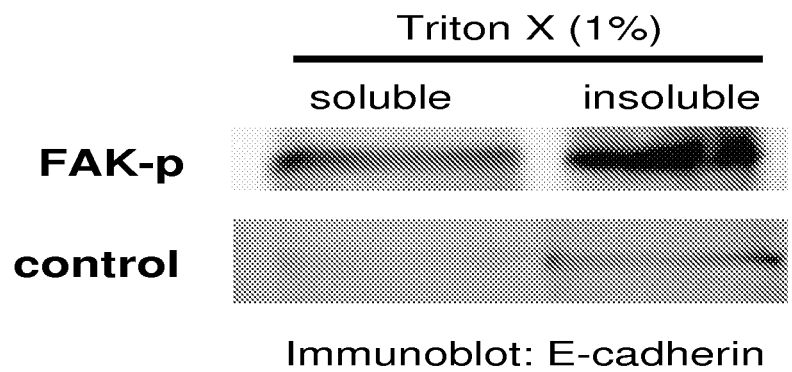
FIG. 11. Membrane insoluble fractions from FAKp⁻loaded lungs show increased E-cadherin. In FAKp-loaded mouse lungs the E-cadherin band was more prominent in the triton-insoluble than the triton-soluble fraction, showing that FAKp induced E-cadherin translocation to the membrane.
Figure 12:
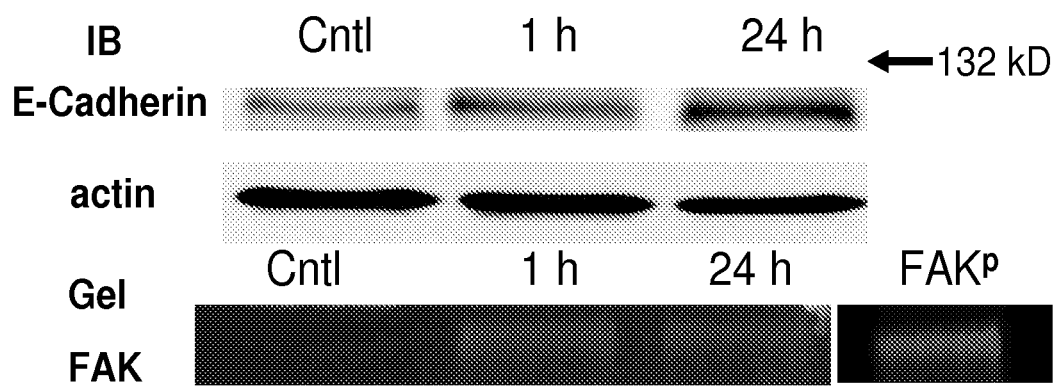
FIG. 12. Immunoblots for E-cadherin on tissue from FAKp loaded lungs. Immunoblots showed increases of E-cadherin at 1 and 24 h after FAKp loading.

In another in vivo experiment we measured paxillin immunoprecipitation in lung tissue one hour after BODIPY-FAKp-Chariot© was infused into mouse tail vein. We found that immunoprecipitation of paxillin also pulled down FAKp (FIG. 10), indicating that FAKp co-associated intracellularly with paxillin. BODIPY fluorescence in the gel confirmed FAKp uptake by lung tissue. Fractionation of FAKp-loaded mouse lungs showed that the E-cadherin band was more prominent in the triton-insoluble fraction than the triton-soluble fraction, which means that FAKp induced E-cadherin translocation from the cytoplasm to the membrane. (FIG. 11). Immunoblots of E-cadherin and FAKp in lung homogenate lysates from the same perfused lungs showed a 50% increase of E-cadherin 1 hour after FAKp infusion, and a 150% increase after 24 hours (FIG. 12). The 1 hour result may reflect E-cadherin translocation from the cytosol to the membrane, although there is a possibility that transcription increased the protein content. These data are the first evidence showing that exogenously added active FAK (FAKp) is taken up intracellularly and that it establishes protein/protein interaction with a major focal adhesion protein E-cadherin.

FAKp Increases Capillary E Cadherin Expression In Situ.

Figure 13:
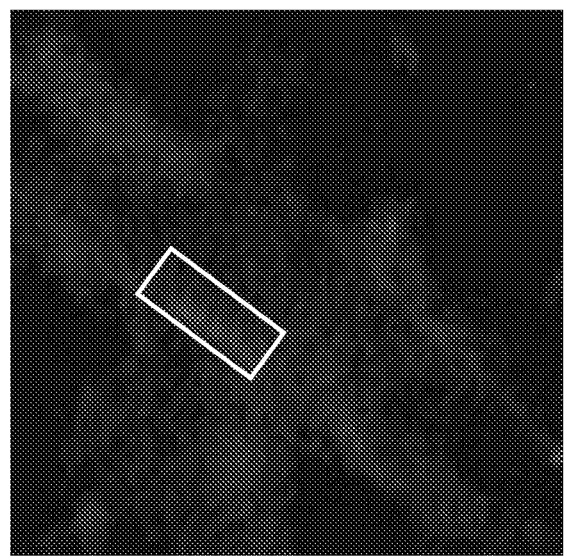
FIG. 13. Endothelial staining of E-cadherin in a control capillary. In-situ immunofluorescence showing E-cadherin staining in a lung capillary.
Figure 14:
FIG. 14. Endothelial staining of E-cadherin in a FAKp-loaded capillary. In-situ immunofluorescence showing E-cadherin staining in a lung capillary after intravenous infusion of FAKp.
Figure 15:
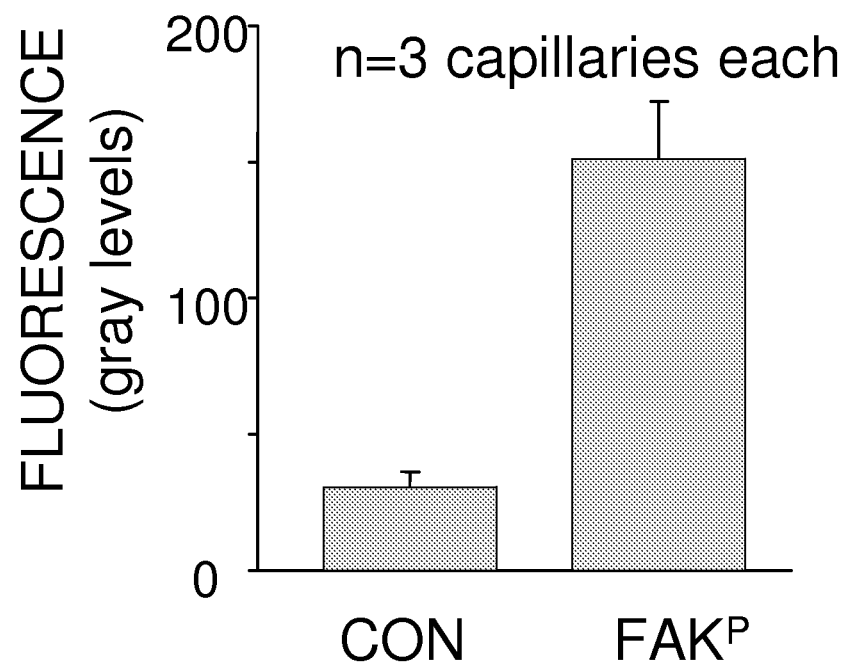
FIG. 15. Endothelial E-cadherin fluorescence. E-cadherin fluorescence was increased >3 fold above control levels in capillaries loaded with FAKp (n=3, *p<0.05, FAKp>control).

To detect E-cadherin expression in FAKp loaded capillaries, we applied the described in situ immunofluorescence methods. First a primary and then a fluorescent secondary anti-E-cadherin monoclonal antibody (mAb) were sequentially injected into microvessels of the isolated blood-perfused lung; then the capillaries were washed with buffer to remove unbound mAb. E-cadherin fluorescence was weak in control capillaries (FIG. 13), but bright in FAKp-loaded capillaries (FIG. 14) which showed a three-fold increase in fluorescence compared to controls ($P<0.05$) (FIG. 15). These findings show that activated FAKp increases the expression of endothelial cell E-cadherin.

FAKp Effects Decreases Capillary Permeability.

Figure 16:
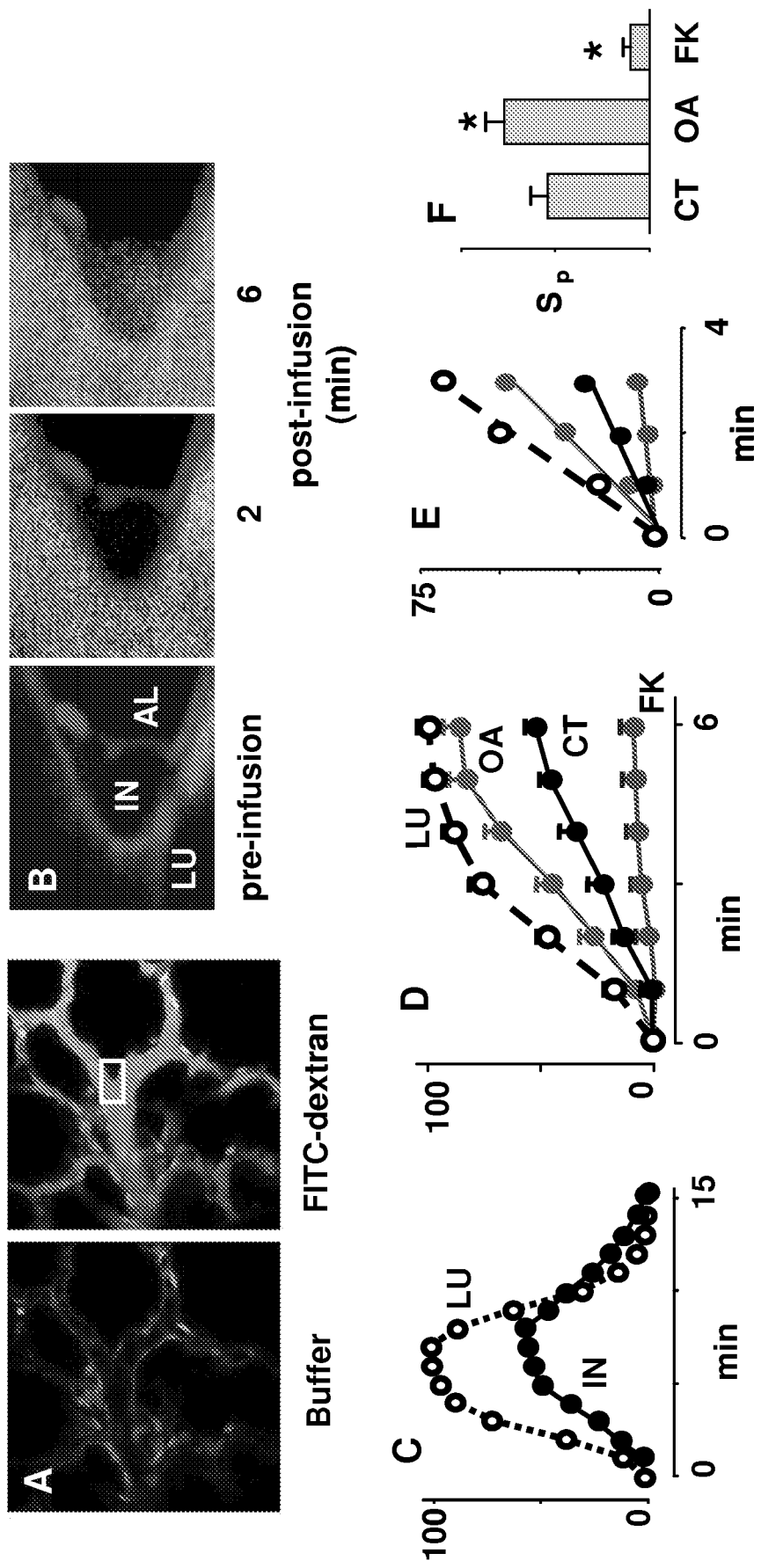
FIG. 16. Assessment of endothelial permeability by 2-photon microscopy. To determine EC barrier responses in FAKp-loaded capillaries, capillaries were microinfused with the tracer FITC-dextran A. Left: endothelium loaded with cytosolic dye calcein-red. Right: intraluminal FITC-dextran (green). B. Vessel bifurcation (white box in A) shown at high magnification pre- and post-FITC dextran infusion. C. Single tracings of luminal (LU) and interstitial (IN) fluorescence. The group data (n=3 for each) (D) show that oleic acid (OA) augmented the increase of interstitial fluorescence, while FAKp loading decreased it. E. Linear regression plots of the data obtained in the first 3 minutes of infusion (D). The rate of increase of interstitial fluorescence, $dCi/dt$ was determined from the slope of the regression plot. F. Capillary permeability to dextran (Sp) was determined from the relation $Sp = (Wi*dCi/dt)/(Cv-Ci)$. Cv and Ci were determined at 2 min. N=3 for each. $P<0.05$ compared with CT (*). The permeability agonist, oleic acid increased Sp to $4.3\pm0.8$ ($P<0.05$; n=3).

To determine EC barrier responses in FAKp-loaded capillaries, we developed a new method for quantifying microvascular permeability using two-photon microscopy, which has the advantage of permitting quantification of tracer uptake across a thin optical section of the tissue under spatially determined conditions. Capillaries in isolated blood-perfused lungs were microinfused with the tracer FITC-dextran (molecular weight 20 Kilodaltons; 0.5 mg/ml; 1 ml/h) (FIG. 16A), and intraluminal (Cv) and interstitial (Ci) fluorescence in the tissue space lying between the vessel bifurcation and an alveolar corner was continuously determined (FIG. 16B). As expected, intraluminal fluorescence increased faster than interstitial fluorescence (FIG. 16C). As expected, the group data (n=3 for each) (FIG. 16D) show that permeability agonist oleic acid (OA) augmented the increase of interstitial fluorescence, while FAKp administration decreased it. We determined the interstitial width, Wi (FIG. 16B). Using linear regression analyses of the data during the first 3 minutes of FAKp infusion (FIG. 16E), we determined the rate of increase of interstitial fluorescence as the regression slope, $dCi/dt$. Then, we estimated solute (dextran) permeability (SP) at the 2 minute point from the relation $Sp=(Wi*dCi/dt)/(Cv-Ci)$. Cv and Ci were also determined at 2 minutes. The bar graph (FIG. 16F) shows that Sp was $2\pm0.7\times10-6$ (SE) cm/sec at baseline (n=3), and oleic acid caused more than a two-fold increase in Sp to $4.3\pm0.8$ ($P<0.05$; n=3). By contrast, FAKp loading caused a ten-fold? Decrease in Sp from $2\pm0.7\times10-6$ (SE) cm/sec to $0.2\pm0.2$ ($P<0.05$; n=3), showing that FAKp increased EC barrier enhancement.

FAKp Administration In Vivo Prevents ALI

Despite high mortality and morbidity in ALI and ARDS, specific barrier enhancement therapy is still lacking In ALI, EC barrier deterioration causes pulmonary edema. Hence, rebuilding barrier enhancement or preventing barrier breakdown has much needed therapeutic use.

To determine global permeability responses in the lungs, we administered intratracheal acid instillation (2 ml/kg, HCl pH 1.5) to the anesthetized mouse to induce ALI. Two hours later, the lungs were removed and the filtration coefficient Kf was quantified using standard approaches (6). FIG. 17 shows that Kf was ~0.3 units at baseline before acid administration (white bar), and it more than doubled after acid treatment, indicating the onset of microvascular injury (black bar=post injury Kf; * means a statistically significant difference from the baseline value). Intravascular injection (in the tail vein) of FAKp-Chariot© (500 micrograms/kilogram (0.5 mg·kg) body weight) about 30 minutes after acid instillation, completely abrogated the Kf increase caused by the acid in untreated controls (grey bar). This result shows that postinjury treatment with FAKp blocks acid-induced lung injury. See also FIG. 18.

In a second experiment, FAKp was administered as above, except that it was administered 24 hours before intratracheal acid administration (FIG. 19, grey bar). FAKp administration markedly reduced by about 70% the acid-induced injury showing that the protective effect of FAKp lasts at least 24 hours.

These results taken together show that administering FAKp to an animal either at risk of developing ALI or having ALI prevents lung damage by strengthening the microvascular EC barrier, or restoring the barrier even after damage had already occurred.

Method of Attaching a Therapeutic Cargo Protein or Peptide to a Transport Protein Most of the known methods for delivering a cargo protein such as FAKp to a target cell involve either fusing the cargo to a transport protein that facilitates uptake of the cargo protein, transcribing the transport protein and cargo protein together into a single fusion protein, or covalently linking the cargo and transport proteins. Either way, instead of delivering the cargo protein as a separate entity, the cargo protein remains bound to the transport protein inside the cell. It is possible in some situations that the presence of the transport protein bound to the cargo protein could reduce the biological activity of the therapeutic cargo protein (in this case FAKp), or interfere with its metabolism in the cell. Fortunately, the experiments described above showed that FAKp covalently bound to Chariot© was still able to enhance EC barrier function. We have discovered a new method for linking FAKp to a transport protein through a non-covalent linkage that is broken once the complex passes through the target cell membrane, thereby releasing the cargo FAKp intact to more accurately mimic normal, endogenous FAKp.

Recent studies have demonstrated that proteins and peptides can be delivered intracellularly if conjugated to the protein transduction domain (PTD) of the HIV-1 transcription-activating factor (TAT) (1-6). Hydrophobic biological membranes restrict the passage of hydrophilic molecules such as proteins. However, since TAT translocates across biological membranes, fusion protein constructs with TAT have been used to achieve intracellular delivery of various cargo molecules (7). We discovered a new method for modifying a transport protein such as TAT so that it noncovalently binds to any cargo protein, peptide or other molecule that has a histidine tag on it by exploiting the known affinity of a metal such as copper, zinc, cobalt and nickel for histidine.

In the new method a metal ion (in the example it is copper) is first chelated onto one end (preferably the N-terminal end) of the transport protein (such as TAT). When the transport protein-metal molecule is mixed with a cargo protein having a histidine tag, the metal atom binds noncovalently to the histidine tag to make a complex: [Transport Protein-Chelator-Metal]-[Histidine-Cargo Protein]. Most proteins are isolated and purified by adding a histidine tag onto the protein, either through chemical means or using recombinant technology, therefore this new technology is remarkably convenient. In a preferred embodiment the histidine tag is about six histidines long, but a person of skill in the art may be able to adapt the protocol so that fewer, or more histidines will work.

The metal (Cu, Ni, Zn, Co)-histidine bond is a reversible bond that is pH-dependent. At physiological pH (7.4), this bond results from electron-sharing between histidine's imidazole nitrogen and the metal. However, at the significantly lower intracellular pH of 6.8 (Wadsworth S, et al., Am J. Physiol. 1996 July; 271(1 Pt 1):L106-13), the imidazole nitrogen is protonated (bound to hydrogen) thereby producing a positively-charged ammonium ion that is now repelled by the positively-charged metal. This repulsion causes the histidine-tagged cargo protein (such as FAKp) to detach from the metal, thereby releasing it from the transport protein intact in the cytoplasm. A person of skill in the art may modify other metals to be suitable for reversibly linking histidine to the metal. As used herein, it is a metal "ion" when the metal reacts with the chelator, and it is the metal "atom" when the chelated metal reacts with the Histidine tag.

To make a TAT-metal-histidine-FAKp complex, we first linked the chelator, nitrilotriacetic acid (NTA) to the N-terminus of TAT (CHI Scientific, Maynard, Mass.) to make NTA-TAT using methods known in the art (Atherton E, Shepperd R C. 1989. Solid phase peptide synthesis, a practical approach, IRL press, Oxford, incorporated herein by reference). Any method known in the art can be used to add a metal chelating agent to the transport protein. We then mixed equimolar amounts of NTA-TAT (500 uM in 20 uL sterile buffer) and copper sulfate (500 uM in 20 uL deionized water) for 30 minutes at room temperature. Finally, the resulting copper-containing NTA-TAT was mixed with his-FAKp, also at room temperature. In this final mixture, component volumes were adjusted to establish concentrations of NTA-TAT at 50 micromolar and of his-FAKp at experimentally required levels (5-100 microgram/ml). The final product is a TAT-(chelator, NTA)-Cu-histidine-FAKp complex. A person of skill in the art of medicinal chemistry will know how to customize this basic protocol for various combinations of chelators, metals (including copper, zinc, nickel or cobalt), cargo proteins and transport proteins. Among the chelators that can be used to bind a metal ion to a transport protein are EDTA, Dimercaptosuccinic acid (DMSA), 2,3 Dimercapto-1-propanesulfonic acid (DMPS), and alpha lipoic acid (ALA). Any transport known in the art can be used. Some common transport proteins are listed below.

Using the above-described methods, a person of skill in the art can link more than one cargo protein to a single transport protein or peptide. For example one can chelate a metal ion onto the N-terminus of TAT as described above to make TAT-using the chelating agent NTA (chelator, NTA)-metal, and one can also chelate a metal ion onto a first histidine-tagged protein (Protein 1) on the end of the protein that does not have the histidine tag to make his-Protein1-(chelator, NTA)-metal. When these two complexes are mixed with a second histidine tagged protein (Protein 1) the following complex is formed:

TAT-[NTA-Metal]-histidine-Protein 1-[NTA-Metal]-histidine-Protein 2

Routine experimentation will identify the best combinations of transport and cargo proteins and may place limits on the size or number of the cargo proteins that can be linked to a single transport protein. This new technology not only makes it possible to deliver a protein to a target cell in free form (unbound to the transport protein), but it makes it possible to deliver two or more proteins (or peptides) at once. Protein 1 and Protein 2 can be the same or different proteins. Certain embodiments of the invention include the following:

1. A transport protein (such as TAT), one end of which is chelated to a metal ion such as copper, nickel, zinc or cobalt, preferably the N-terminal end. The transport protein is covalently bound to a chelating agent (such as NTA) at one end, and the chelating agent is covalently bound to the metal making. Transport Protein-[chelating agent-metal]

2. A cargo protein intended for delivery to a target cell that has a histidine tag at one end and a chelating agent that is capable of binding to one or more of the following metals: copper, nickel, zinc and cobalt at the other end. This molecule can be used to bind a second cargo protein (that is the same or different) to facilitate attaching two cargo proteins to a single transport protein: Histidine tag-Protein 1-[chelating agent (such as NTA)]

3. The complex in item two, wherein the chelating agent is covalently bound to a metal ion that is one of copper, nickel, zinc and cobalt: Histidine tag-Protein 1-[NTA-metal].

4. A complex that includes a transport protein bound to a first protein intended for delivery to a target cell, having the composition: Transport Protein-[first chelating agent-first metal]-histidine tag-Protein 1. The transport protein is covalently bound to the first chelating agent, which first chelating agent is covalently bound to the first metal, which first metal is noncovalently bound to the histidine tag on Protein 1.

5. The complex of item four, in which the free end of Protein 1 is bound to a second chelating agent (that can be the same or different from the first), and preferably in which the chelating agent is bound to a metal ion that is one of copper, nickel, zinc and cobalt:

Transport Protein-[first chelating agent-first Metal]-histidine tag-Protein 1-[second chelating agent-second metal]

6. A complex that includes a transport protein and two proteins intended for delivery to a target cell, wherein the proteins can be the same or different, having the composition: Transport Protein-[first chelating agent-first Metal]-histidine tag-Protein 1-[second chelating agent-second metal]-histidine tag-Protein 2 and in which the transport protein is covalently bound to the first chelating agent, which first chelating agent is covalently bound to the first metal, which first metal is non-covalently bound to the histidine tag on Protein 1, and in which Protein 1 is covalently bound to the second chelating agent, which second chelating agent is covalently bound to the second metal, which second metal is noncovalently bound to the histidine tag on Protein 2, And in which the first and second chelating agents, the first and second metals and the first and second proteins can be the same or different.

7. A kit comprising any of the items in 1-6 or combinations thereof. A preferred kit includes the molecule described in item 1, which is ready for mixing with a histidine-tagged cargo protein (intended for delivery to a target cell) for which the transport protein will facilitate cargo protein uptake. Another kit includes item 1 and item 3, which when mixed together form:

Transport Protein-[first chelating agent-first Metal]-histidine tag-Protein 1-[second chelating agent-second metal]. This molecule is ready for attaching a second protein that is the same or different from protein 1 to the metal atom on the free end of the first protein.

Some of the transport proteins known to enhance uptake of a therapeutic agent include, but are not limited to the following:

```
Protein-derived peptides
Penetratin
                                   SEQ ID NO: 1
RQIKIWFQNRRMKWKK Tat fragment (48-60)
                                   SEQ ID NO: 2
GRKKRRQRRRPPQ *b Signal-sequence-based peptides (I)
                                   SEQ ID NO: 3
GALFLGWLGAAGSTMGAWSQPKKKRKV *c Signal-sequence-based peptides (II)
                                   SEQ ID NO: 4
AAVALLPAVLLALLAP Synthetic or chimeric peptides
Transportan
                                   SEQ ID NO: 5
GWTLNSAGYLLKINLKALAALAKKIL Amphiphilic model peptide
                                   SEQ ID NO: 6
KLALKLALKALKAALKLA
``` a. The peptide families are represented by the original sequence; for analogue sequences see M. Lindgren et al., TiPS-March 2000 (Vol. 21) 99.
b. This sequence is included in all Tat fragments with known translocation ability [e.g. Tat fragment (37-72) that has been used for intracellular protein delivery; see Table 1]. It should be noted that the Tat protein has a high genetic variability so the exact amino acid sequence might differ depending on viral strain.
c. MPS peptide, a chimera of the hydrophobic terminal domain of the viral gp41 protein and the nuclear localization signal (NLS) from Simian virus 40 large antigen, which is one example of a possible combination of NLSs and membrane translocating sequences (MTSs) that have been shown to internalize independent of temperature, and function as a carrier for oligonucleotides (20).

Any protein or peptide or other molecule that has a histidine tag on it can be linked to a transport protein as described above. In an embodiment, toxic proteins, peptides or other molecules modified to have a histidine tag on them, can be bound to a transport protein to which a metal from the group Cu, Zn, Co and Ni has been chelated for targeted delivery to cancer cells. In one preferred embodiment, the toxic molecule-transport protein complex includes anti-cancer agents that can be injected locally near the site of a targeted tumor.

Using this new technology, any molecule onto which an appropriate metal can be chelated can be used as a transport molecule for any cargo molecule that has a histidine tag. In an embodiment, a hormone that binds to a hormone receptor on a target cell is adapted by chelating it to an appropriate metal in order to deliver an appropriate histidine-tagged cargo protein/molecule to the targeted cell. Routine experimentation would determine if the cargo protein/molecule internalized by the targeted cell retains its biological activity.

We made fluorescence tagged (Alexa-488) TAT-(NTA-CU]-FAKp (hereafter "TAT-FAKp") and tested its uptake and efficacy in cultured lung endothelial cell (EC) monolayers. FIG. 22 shows an image taken by conventional fluorescence microscopy 40 minutes after adding 5 micrograms/ml TAT-FAKp. EC engineered to express green fluorescent protein (GFP) are demarcated by green borders. The red fluorescence within the cell margins denotes intracellular uptake of TAT-FAKp.

Total Internal Reflection Fluorescence (TIRF) microscopy allows visualization of a thin slice of the abluminal cell membrane, namely the membrane that lies adjacent to the glass cover slip on which the cells are grown. In the TIRF image shown in FIG. 23, FAKp expression is evident as red dots interspersed among the green basal membranes of GFP-labeled EC. This dotted distribution attests to incorporation of FAKp in structures called focal adhesions that form attachments of the cell membrane to the underlying matrix. This distribution indicates that TAT-FAKp is taken up by cultured endothelial cells. We know that FAKp is released from TAT at intracellular pH, and the results show that it localizes to focal adhesions.

To determine efficacy of uptake in living lung microvessels, we injected TAT-FAKp at a concentration of 5 micrograms/ml in blood perfusing an isolated mouse lung. The low power (FIG. 24) and high power (FIG. 25) fluorescence images of microvessels show the red fluorescence that indicates TAT-FAKp uptake in lung microvessels 40 minutes after TAT-FAKp injection. Together, the monolayer and the mouse lung studies show that lung endothelial cells internalize TAT-FAKp, that FAKp is released, and that it localizes to focal adhesions.

To determine whether intravenously injected TAT-FAKp protects against acute lung injury (ALI), we used our in vivo acid instillation model of ALI in the mouse. Either 0.1N hydrochloric acid or saline (control) were instilled intra-tracheally, then after 4 hours blood-free extravascular lung water (EVLW) was analyzed. As shown in FIG. 26, EVLW increased significantly in untreated control animals after acid instillation, indicating presence of ALI. However TAT-FAKp given by tail vein injection 30 minutes after acid instillation (500 microgram/kilogram of body weight in 150 microliters) abrogated the EVLW increase. This shows that uptake of TAT-FAKp in endothelial cells of lung microvessels blocked acid-induced ALI in vivo.

Based on the results of the experiments described above, certain embodiments of the invention are directed to methods for treating or preventing ALI and ARDS in an animal, preferably a human that is at risk or that has the disease by administering a therapeutically effective amount of activated FAKp. The animal is preferably a human, and FAKp is preferably human recombinant FAKp. In a preferred embodiment the FAKp is bound to a transport protein that facilitates its uptake into lung EC. In a preferred embodiment FAKp is non-covalently bound to a transport protein that facilitates its uptake by a target lung EC using a metal linkage as described above. The transport protein is preferably TAT or Chariot©, but it can be any transport protein. FAKp can be administered prophylactically to prevent ALI or ARDS in a subject up to 24 hours before the subject is subjected to a situation that poses a heightened risk of developing ALI or ARDS, or it can be administered to treat a patient having one of these diseases to minimize damage to the lungs.

In an embodiment of the invention, the therapeutically effective amount of FAKp is in the range of between about 0.1-20 mg/kg body weight, preferably about 0.5 mg/kg, as needed to normalize or maintain lung function. We used 500 micrograms/kg (or 0.5 mg/kg) of recombinant, isolated and purified FAKp for the in vivo experiments. Therefore this is a good starting place for determining the ideal dose in humans or other mammals. A skilled physician will know how often, at what strength and for how long FAKp should be administered to a patient at risk of developing or in need of treatment for ALI or ARDS. Preferred routes of administration include targeted delivery to the lungs for example through inhalation, or alternatively by intravenous injection.

Effect of Hyperosmolar Sucrose on ALI.

Figure 21:
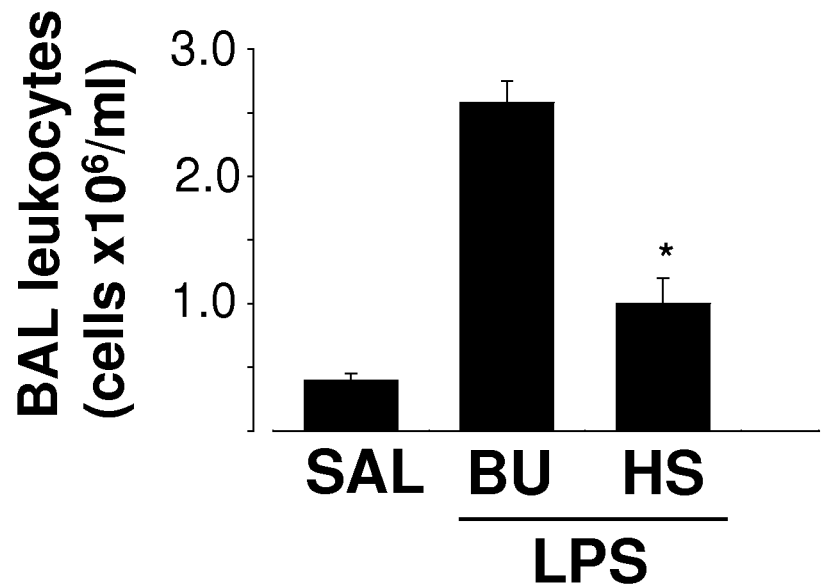
Figure 21:
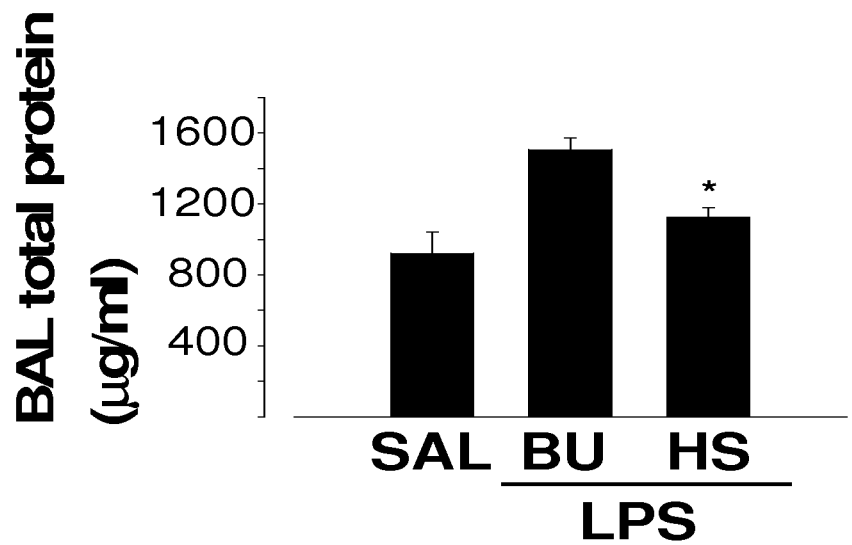

We recently reported that hyperosmolar sucrose enhances lung microvascular barrier properties by activating focal adhesion kinase (FAKp), thereby blocking pulmonary edema in acute lung injury (ALI). (6) To determine protection in the long term, we administered intra-tracheal acid instillation (2 ml/kg, HCl pH 1.5) to anesthetized rats. After the rats recovered from anesthesia, we determined extravascular lung water content (EVLW) at different durations for 24 hours. We saw that EVLW increased to a high level at 2 hours following acid-induced ALI, and this level was maintained for 24 hours (FIG. 20). Hyperosmolar sucrose given intravenously 30 minutes after acid instillation reversed ALI. In other experiments, we gave intra-tracheal buffer or LPS to rats. After 24 h, we obtained broncho-alveolus lavage (BAL) samples. BAL leukocyte counts and protein content were markedly elevated for buffer instilled rats (FIG. 21 A,B). However, in rats given LPS instillation followed by intravenous hyperosmolar sucrose 30 minute later, both BAL measures were markedly inhibited (FIG. 22 A,B) indicating protection against ALI. Hyperosmolar sucrose blocked LPS-induced lung inflammation and protein leak.

Therefore, certain embodiments of the invention are directed to treatment or prevention of ALI or ARDS by administering a combination therapy of FAKp (preferably conjugated to a transport protein, and preferably intravenous or inhalation administration) and hyperosmolar sucrose (preferably intravenously administered), either in the same preparation or in different preparations, either on the same day or on different days.

Treatment of Diseases Associated with Reduced E Cadherin Junctions

Other embodiments of the invention are directed to methods for treating other diseases associated with reduced E cadherin junctions, including edema such as pulmonary or cerebral edema, tumor metastasis, inflammatory condition including sepsis, arthritis, hepatitis, nephritis, hyaline membrane disease, and cerebral inflammation (tightened junctions will prevent the underlying leukocyte migration thus reduce inflammation), and neonatal bronchopulmonary dysplasia, by administering a therapeutically effective amount of activated FAKp to a patient in need of such treatment.

An embodiment of the invention is directed to a method of treating tumor metastasis by administering a therapeutically effective amount of activated FAKp to a cancer patient. By strengthening the endothelial barrier by increasing E cadherin, FAKp can reduce migration of cancer cells across the vascular wall.

Pharmaceutical Formulations

The compounds of this invention can be formulated and administered to prevent or treat ALI or ARDS is by any means that produces contact of the active ingredient with the agent's site of action in the body of a mammal, preferably the lungs. In a preferred embodiment a therapeutically effective amount of the drug FAKp (alone or conjugated to a transport protein) is administered to a patient in need of treatment for ALI, ARDS or other disease related to reduced E-cadherin at EC junctions or decreased EC barrier function. The route of administration can be any route that delivers the therapeutic agent to the intended target, preferably by inhalation or injection. FAKp can be administered together with hyperosmolar sucrose, but can also be administered separately. FAKp can be administered alone, but is preferably administered with a pharmaceutical carrier selected on the basis of the chosen route of administration and standard pharmaceutical practice.

The dosage administered will be a therapeutically effective amount of the compound sufficient to result in amelioration of one or more symptoms of the ARDS or ALI or other disease as described herein, and will vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired. Treatment of a subject with a therapeutically effective amount of FAKp can include a single treatment or, preferably a series of treatments. We used 500 micrograms/kg (or 0.5 mg/kg) isolated and purified FAKp for our in vivo experiments. Therefore this is a good starting place for determining the ideal dose in humans or other mammals. In a preferred embodiment the protein or polypeptide the therapeutically effective amount is in the range of between about 0.1-20 mg/kg body weight, preferably about 0.5 mg/kg, as needed to normalize or maintain lung function.

The efficacy of the activated FAKp can be determined by monitoring the indicia of ALI and ARDS or other lung diseases, for example using a chest X-ray to monitor pulmonary edema or by measuring the partial arterial pressure of oxygen. (Wheeler A P, G R Bernard. Acute lung injury and the acute respiratory distress syndrome: a clinical review. The Lancet, 2007. 369:1553-1564). When hypoxia from acute lung injury is severe, (the partial arterial pressure of oxygen $PaO_2$/fractional concentration of oxygen in inspired air $F_1/O_2$ is less than about 200), the disorder is termed ARDS. However most epidemiological and interventional studies use the broader range of gas exchange abnormality $PaO2/F_1O_2<300$ and refer to the overall disorder as acute lung injury ALI.

Toxicity and therapeutic efficacy of FAKp can be determined by standard pharmaceutical procedures for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

Formulations and Use

Pharmaceutical compositions for use in accordance with the present invention may be formulated in the conventional manner using one or more physiologically acceptable carriers or excipients. Thus, the compounds and their physiologically acceptable salts and solvates may be formulated for administration by inhalation or insufflation (either through the mouth or the nose) or oral, buccal, or parenteral administration. For administration by inhalation, a preferred embodiment for delivering drugs to the lungs, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. In general, water, suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

A composition of the present invention can also be formulated as a sustained and/or timed release formulation. Such sustained and/or timed release formulations may be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the present invention can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

Standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

A parenteral composition suitable for administration by injection can be prepared by stirring 1.5% by weight of active ingredients in 10% by volume propylene glycol and water. The solution is made isotonic with sodium chloride and sterilized.

Suspension: An aqueous suspension can be prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

Accordingly, the pharmaceutical composition of the present invention may be delivered via various routes and to various sites in an animal body to achieve a particular effect (see, e.g., Rosenfeld et al., 1991, supra; Rosenfeld et al., 1991, Clin. Res., 39(2), 311A; Jaffe et al., supra; and Berkner, supra). One skilled in the art will recognize that although more than one route can be used for administration, a particular route can provide a more immediate and more effective reaction than another route. Local or systemic delivery can be accomplished by-administration comprising application or instillation of the formulation into body cavities, inhalation or insufflation of an aerosol, or by parenteral introduction, comprising intramuscular, intravenous, peritoneal, subcutaneous, intradermal, as well as topical administration.

These methods described herein are by no means all-inclusive, and further methods to suit the specific application will be apparent to the ordinary skilled artisan. Moreover, the effective amount of the compositions can be further approximated through analogy to compounds known to exert the desired effect.

The actual dose and schedule can vary depending on whether the compositions are administered in combination with other pharmaceutical compositions, or on differences between individual in pharmacokinetics, drug disposition, and metabolism. One skilled in the art can easily make any necessary adjustments in accordance with the exigencies of the particular situation.

Protein Variants.

Variants of FAK and FAKp for therapeutic use as described herein, include proteins substantially homologous to FAK and FAKp but derived from another organism, i.e., an ortholog. Variants also include proteins that are substantially homologous to FAK and FAKp that are produced by chemical synthesis, that are isolated and purified from an animal or bacterium or that are produced by recombinant methods.

As used herein, two proteins (or a region of the proteins) are substantially homologous when the amino acid sequences are at least about 70-75%, typically at least about 80-85%, and most typically at least about 90-95%, 97%, 98% or 99% or more homologous. A substantially homologous amino acid sequence, according to the present invention, will be encoded by a nucleic acid sequence hybridizing to the corresponding nucleic acid sequence, or portion thereof, under stringent conditions as more fully described below.

A variant polypeptide can differ in amino acid sequence by one or more substitutions, deletions, insertions, inversions, fusions, and truncations or a combination of any of these. Fully functional variants typically contain only conservative variation or variation in non-critical residues or in non-critical regions. Functional variants can also contain substitution of similar amino acids, which results in no change or an insignificant change in function.

As indicated, variants can be naturally-occurring or can be made by recombinant means of chemical synthesis to provide useful and novel characteristics of the desired protein. This includes preventing immunogenicity from pharmaceutical formulations by preventing protein aggregation.

Substantial homology can be to the entire amino acid sequence or to fragments of these sequences. Fragments can be derived from the full naturally occurring amino acid sequence. However, the invention also encompasses biologically active fragments of the variants. Accordingly, a fragment can comprise any length that retains one or more of the biological activities of the FAKp, for example the ability to increase EC barrier function. Fragments can be discrete (not fused to other amino acids or polypeptides) or can be within a larger polypeptide. Further, several fragments can be comprised within a single larger polypeptide.

FAK and FAKp can be produced by any conventional means (Houghten, R. A. (1985) Proc. Natl. Acad. Sci. USA 82:5131-5135) including chemical synthesis and recombinant technology as described in Example 1. Simultaneous multiple peptide synthesis is described in U.S. Pat. No. 4,631, 211.

Variants of FAK and FAKp include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretary sequence, or a sequence facilitating purification. Such variant polypeptides are deemed to be within the scope of those skilled in the art from the teachings herein. For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity; see, e.g. Pinckard, Clin. Exp. Immunol. 2 (1967), 331-340: Bobbins, Diabetes 36 (1987), 838-845; Cleland. Crit. Rev. Therapeutic Drug Carrier Systems 10 (1993), 307-377.

"Amino acid residue" (including those making up FAKp) refers to an amino acid which is part of a polypeptide. The amino acid residues described herein are preferably in the L" isomeric form. However, residues in the D" isomeric form can be substituted for any L-amino acid residue, as long as the desired functional property is retained by the polypeptide. $NH_2$ refers to the free amino group present at the amino terminus of a polypeptide. COOH refers to the free carboxyl group present at the carboxyl terminus of a polypeptide. "Amino acid residue" is broadly defined to include the 20 amino acids commonly found in natural proteins, as well as modified and unusual amino acids, such as those referred to in 37 C.F.R. Sections 1.821-1.822, and incorporated herein by reference. In a peptide or protein, suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224).

Many amino acids, including the terminal amino acids, may be modified by natural processes, such as processing and other post-translational modifications, or by chemical modification techniques well known in the art. Common modifications that occur naturally in polypeptides are described below.

Protein Modifications

FAK and FAKp, and their biologically active analogs, derivatives, fragments and variants for use in the present invention can be modified according to known methods in medicinal chemistry to increase its stability, half-life, uptake or efficacy. Certain known modifications are described below.

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the amino terminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells, and, for this reason, insect cell expression systems have been developed to efficiently express mammalian proteins having native patterns of glycosylation. Similar considerations apply to other modifications. The same type of modification may be present in the same or varying degree at several sites in a given polypeptide. Also, a given polypeptide may contain more than one type of modification.

FAK and FAKp can be isolated and purified from cells that naturally express it, or from transformed cells that have been modified to overproduce it, or it can be synthesized using known protein synthesis methods.

| Protein Modification | Description |
| --- | --- |
| Acetylation | Acetylation of N-terminus or e-lysines. Introducing an acetyl group into a protein, specifically, the substitution of an acetyl group for an active hydrogen atom.<br>A reaction involving the replacement of the hydrogen atom of a hydroxyl group with an acetyl group ($CH_3CO$) yields a specific ester, the acetate. Acetic anhydride is commonly used as an acetylating agent, which reacts with free hydroxyl groups. Acylation may facilitate addition of other functional groups. A common reaction is acylation of e.g., conserved lysine residues with a biotin appendage. |
| ADP-ribosylation | Covalently linking proteins or other compounds via an arginine-specific reaction. |
| Alkylation | Alkylation is the transfer of an alkyl group from one molecule to another. The alkyl group may be transferred as an alkyl carbocation, a free radical or a carbanion (or their equivalents). Alkylation is accomplished by using certain functional groups such as alkyl electrophiles, alkyl nucleophiles or sometimes alkyl radicals or carbene acceptors. A common example is methylation (usually at a lysine or arginine residue). |
| Amidation | Reductive animation of the N-terminus. Methods for amidation of insulin are described in U.S. Pat. No. 4,489,159. |
| Carbamylation | Nigen et al. describes a method of carbamylating hemoglobin. |
| Carboxylation | Carboxylation typically occurs at the glutamate residues of a protein, which may be catalyzed by a carboxylase enzyme (in the presence of Vitamin K - a cofactor). |
| Citrullination | Citrullination involves the addition of citrulline amino acids to the arginine residues of a protein, which is catalyzed by peptidylarginine deaminase enzymes (PADs). This generally converts a positively charged arginine into a neutral citrulline residue, which may affect the hydrophobicity of the protein (and can lead to unfolding). |
| Condensation of amines with aspartate or glutamate | Such reactions, may be used, e.g., to attach a peptide to other proteins labels. |
| Covalent attachment of flavin | Flavin mononucleotide (FAD) may be covalently attached to serine and/or threonine residues. May be used, e.g., as a light-activated tag. |
| Covalent attachment of heme moiety | A heme moiety is generally a prosthetic group that consists of an iron atom contained in the center of a large heterocyclic organic ring, which is referred to as a porphyrin. The heme moiety may be used, e.g., as a tag for the peptide. |
| Attachment of a nucleotide or nucleotide derivative | May be used as a tag or as a basis for further derivatising a peptide. |
| Cross-linking | Cross-linking is a method of covalently joining two proteins. Cross-linkers contain reactive ends to specific functional groups (primary amines, sulfhydryls, etc.) on proteins or other molecules. Several chemical groups may be targets for reactions in proteins and peptides. For example, Ethylene glycol bis[succinimidylsuccinate, Bis[2-(succinimidooxycarbonyloxy)ethyl]sulfone, and Bis[sulfosuccinimidyl] suberate link amines to amines. |
| Cyclization | For example, cyclization of amino acids to create optimized delivery forms that are resistant to, e.g., aminopeptidases (e.g., formation of pyroglutamate, a cyclized form of glutamic acid). |
| Disulfide bond formation | Disulfide bonds in proteins are formed by thiol-disulfide exchange reactions, particularly between cysteine residues (e.g., formation of cystine). |
| Demethylation | See, e.g., U.S. Pat. No. 4,250,088 (Process for demethylating lignin). |
| Formylation | The addition of a formyl group to, e.g., the N-terminus of a protein. See, e.g., U.S. Pat. Nos. 4,059,589, 4,801,742, and 6,350,902. |
| Glycylation | The covalent linkage of one to more than 40 glycine residues to the tubulin C-terminal tail. |
| Glycosylation | Glycosylation may be used to add saccharides (or polysaccharides) to the hydroxy oxygen atoms of serine and threonine side chains (which is also known as O-linked Glycosylation). Glycosylation may also be used to add saccharides (or polysaccharides) to the amide nitrogen of asparagine side chains (which is also known as N-linked Glycosylation), e.g., via oligosaccharyl transferase. |
| GPI anchor formation | The addition of glycosylphosphatidylinositol to the C-terminus of a protein. GPI anchor formation involves the addition of a hydrophobic phosphatidylinositol group - linked through a carbohydrate containing linker (e.g., glucosamine and mannose linked to phosphoryl ethanolamine residue) - to the C-terminal amino acid of a protein. |
| Hydroxylation | Chemical process that introduces one or more hydroxyl groups (—OH) into a protein (or radical). Hydroxylation reactions are typically catalyzed by hydroxylases. Proline is the principal |

| Protein Modification | Description |
|---|---|
| | residue to be hydroxylated in proteins, which occurs at the $C^\gamma$ atom, forming hydroxyproline (Hyp). In some cases, proline may be hydroxylated at its $C^\beta$ atom. Lysine may also be hydroxylated on its $C^\delta$ atom, forming hydroxylysine (Hyl). These three reactions are catalyzed by large, multi-subunit enzymes known as prolyl 4-hydroxylase, prolyl 3-hydroxylase and lysyl 5-hydroxylase, respectively. These reactions require iron (as well as molecular oxygen and α-ketoglutarate) to carry out the oxidation, and use ascorbic acid to return the iron to its reduced state. |
| Iodination | See, e.g., U.S. Pat. No. 6,303,326 for a disclosure of an enzyme that is capable of iodinating proteins. U.S. Pat. No. 4,448,764 discloses, e.g., a reagent that may be used to iodinate proteins. |
| ISGylation | Covalently linking a peptide to the ISG15 (Interferon-Stimulated Gene 15) protein, for, e.g., modulating immune response. |
| Methylation | Reductive methylation of protein amino acids with formaldehyde and sodium cyanoborohydride has been shown to provide up to 25% yield of N-cyanomethyl (—CH$_2$CN) product. The addition of metal ions, such as Ni$^{2+}$, which complex with free cyanide ions, improves reductive methylation yields by suppressing by-product formation. The N-cyanomethyl group itself, produced in good yield when cyanide ion replaces cyanoborohydride, may have some value as a reversible modifier of amino groups in proteins. (Gidley et al.) Methylation may occur at the arginine and lysine residues of a protein, as well as the N- and C-terminus thereof. |
| Myristoylation | Myristoylation involves the covalent attachment of a myristoyl group (a derivative of myristic acid), via an amide bond, to the alpha-amino group of an N-terminal glycine residue. This addition is catalyzed by the N-myristoyltransferase enzyme. |
| Oxidation | Oxidation of cysteines. Oxidation of N-terminal Serine or Threonine residues (followed by hydrazine or aminooxy condensations). Oxidation of glycosylations (followed by hydrazine or aminooxy condensations). |
| Palmitoylation | Palmitoylation is the attachment of fatty acids, such as palmitic acid, to cysteine residues of proteins. Palmitoylation increases the hydrophobicity of a protein. |
| (Poly)glutamylation | Polyglutamylation occurs at the glutamate residues of a protein. Specifically, the gamma-carboxy group of a glutamate will form a peptide-like bond with the amino group of a free glutamate whose alpha-carboxy group may be extended into a polyglutamate chain. The glutamylation reaction is catalyzed by a glutamylase enzyme (or removed by a deglutamylase enzyme). Polyglutamylation has been carried out at the C-terminus of proteins to add up to about six glutamate residues. Using such a reaction, Tubulin and other proteins can be covalently linked to glutamic acid residues. |
| Phosphopantetheinylation | The addition of a 4'-phosphopantetheinyl group. |
| Phosphorylation | A process for phosphorylation of a protein or peptide by contacting a protein or peptide with phosphoric acid in the presence of a non-aqueous apolar organic solvent and contacting the resultant solution with a dehydrating agent is disclosed e.g., in U.S. Pat. No. 4,534,894. Insulin products are described to be amenable to this process. See, e.g., U.S. Pat. No. 4,534,894. Typically, phosphorylation occurs at the serine, threonine, and tyrosine residues of a protein. |
| Prenylation | Prenylation (or isoprenylation or lipidation) is the addition of hydrophobic molecules to a protein. Protein prenylation involves the transfer of either a farnesyl (linear grouping of three isoprene units) or a geranyl-geranyl moiety to C-terminal cysteine(s) of the target protein. |
| Proteolytic Processing | Processing, e.g., cleavage of a protein at a peptide bond. |
| Selenoylation | The exchange of, e.g., a sulfur atom in the peptide for selenium, using a selenium donor, such as selenophosphate. |
| Sulfation | Processes for sulfating hydroxyl moieties, particularly tertiary amines, are described in, e.g., U.S. Pat. No. 6,452,035. A process for sulphation of a protein or peptide by contacting the protein or peptide with sulphuric acid in the presence of a non-aqueous apolar organic solvent and contacting the resultant solution with a dehydrating agent is disclosed. Insulin products are described to be amenable to this process. See, e.g., U.S. Pat. No. 4,534,894. |
| SUMOylation | Covalently linking a peptide a SUMO (small ubiquitin-related Modifier) protein, for, e.g., stabilizing the peptide. |
| Transglutamination | Covalently linking other protein(s) or chemical groups (e.g., PEG) via a bridge at glutamine residues |

| Protein Modification | Description |
|---|---|
| tRNA-mediated addition of amino acids (e.g., arginylation) | For example, the site-specific modification (insertion) of an amino acid analog into a peptide. |

EXAMPLES

Example 1

Methods

A. Purification of Activated Focal Adhesion Kinase (FAKp)

We used methods known in the art for purifying activated FAKp. First we amplified recombinant Baculovirus containing histidine-tagged cDNA that encodes full-length mouse FAK (gift of Dr. Fumio Matsumura, Rutgers University), which is constitutively phosphorylated at tyrosine 397. The gene sequence, cDNA sequence and amino acid sequence of human FAK are known. The complete cds for Homo sapiens focal adhesion kinase mRNA, is ACCESSION NO: L05186; VERSION L05186.1; which also provides the amino acid sequence. The cDNA for making recombinant FAKp for use in the present invention would be a histidine-tagged cDNA that encodes full-length human FAK that is constitutively phosphorylated at tyrosine 397.

Figure 2:
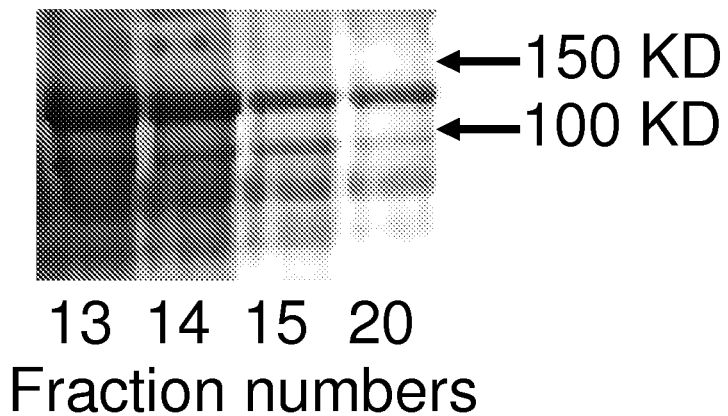
FIG. 2. Coomassie staining of nickel-affinity purified FAKp. FAKp was expressed in insect cells infected with Baculovirus containing cDNA that encodes full-length mouse FAK. FAKp was purified on a nickel-affinity column. Each of fractions 13-20 of the eluate showed one major band on Coomassie staining, indicating the eluate contained one major protein at kD 125, which is the FAK molecular weight.
Figure 3:
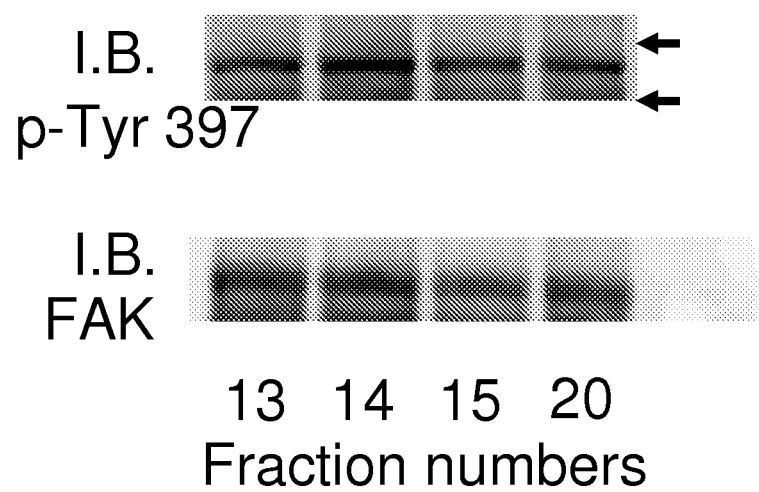
FIG. 3. Immunoblots showing phosphorylated FAK in nickel-affinity column eluate fractions. Immunoblots confirmed both that the protein was tyrosine phosphorylated (upper panel) and that the protein was FAK (lower panel).
Figure 4:
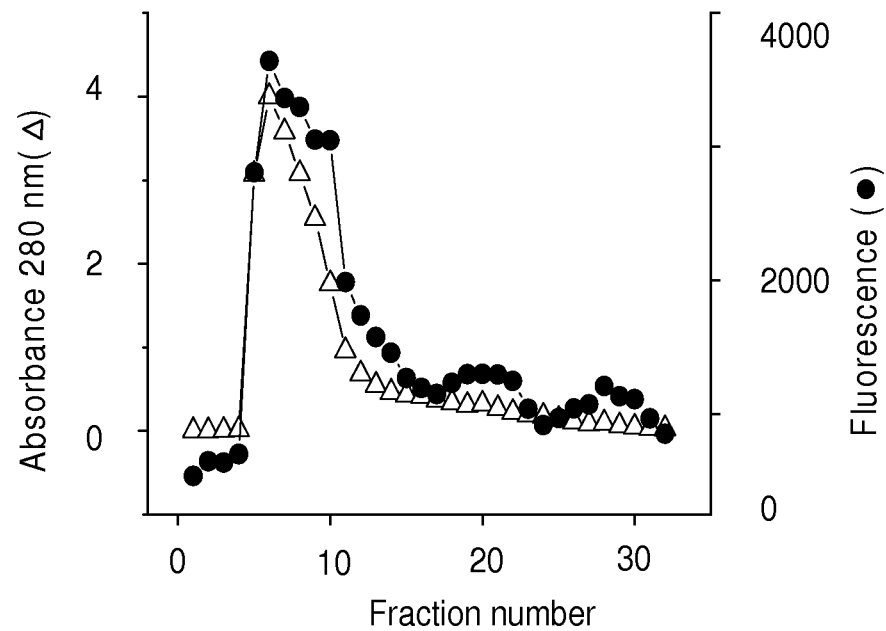
FIG. 4. Nickel column eluate fractions show co-eluation of fractions positive for FAK and fluorescently labeled FAK. For fluorescence labeling, FAKp was covalently linked with BODIPY. FAKp-containing fractions (open circles) co-eluted with BODIPY fluorescence (filled circles, fractions 9-10), when run through a Sephadex-G25 column indicating tight protein-fluorophore linkage. BODIPY fluorescence was absent in protein-free fractions (fractions 20-30), indicating absence of fluorophore leaching from the protein.

We infected insect cells with the virus to express FAKp, which was purified on a nickel affinity column. Each of fractions 13-20 of the eluate showed one major band on Coomassie staining, indicating the eluate contained one major protein at kD 125, which is the FAK molecular weight (FIG. 2). Immunoblots confirmed both that the protein was tyrosine phosphorylated (FIG. 3, upper panel) and that it was FAK (FIG. 3, lower panel). Tyrosine kinase activity of FAK was determined using a tyrosine kinase assay kit from Chemicon. FIG. 2 shows that tyrosine a kinase activity was highest for fraction No. 13, of the nickel column eluate, therefore this fraction was used for the studies described below.

B. Fluorescence Labeling

Figure 5:
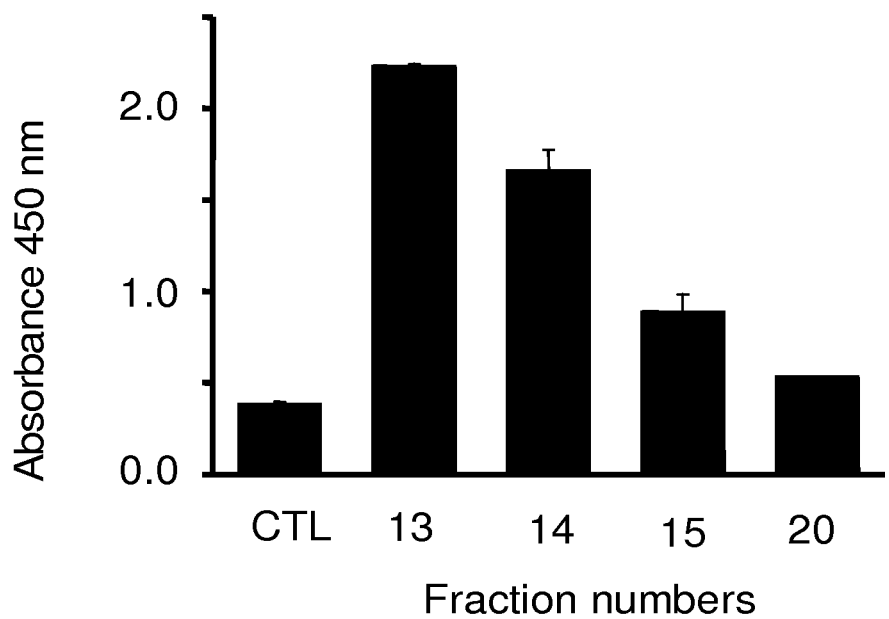
FIG. 5. FAK activity in nickel column eluate fractions. FAKp functionality was assayed in terms of substrate tyrosine phosphorylation, n=3.

FAKp was covalently linked with BODIPY (dipyrromethene boron difluoride) using a commercially available kit (Molecular Probes). To confirm fluorophore-protein binding, we ran samples containing equal protein amounts (BCA assay, Pierce) in a Sephadex-G25 column. FAKp-containing fractions co-eluted with BODIPY fluorescence (FIG. 4, fractions 9-10), indicating tight protein fluorophore linkage. BODIPY fluorescence was absent in protein-free fractions (FIG. 4, fractions 20-30), indicating absence of fluorophore leaching from the protein. These findings indicate that BODIPY was tightly bound to FAKp. Absence of unbound fluorophore indicates that BODIPY did not leach from FAKp. To confirm functionality of FAKp, we assayed its tyrosine kinase activity in terms of substrate tyrosine phosphorylation using a commercially available tyrosine kinase assay kit (Chemicon). Activity was highest for fraction #13 of the nickel-column eluate (FIG. 5). We used this fraction for the studies indicated below. Since FAK activity in fraction #20 is not higher than control (FIG. 5), we used this fraction as our control.

C. Cultured lung microvascular endothelial cells. Methods using rat lung microvascular EC(RLMEC) have been published several times (1, 19, 65, 66). For EC barrier quantification, we determine trans-endothelial resistance (TER) in monolayers grown on sterile polycarbonate inserts held at 37° C. (Endohm, World Precision Instruments).

D. Isolated Blood-perfused Lung.

Our methods have been reported many times. Lungs removed from anesthetized rats or mice (isoflurane inhalation followed by sodium pentobarbital, 50 mg/kg intraperitoneal) are pump-perfused (rat: 10-15 ml/min, mouse: 2-5 ml/min) with autologous blood at constant pressures (pressure transducer, P23 ID Gould Statham) in the pulmonary artery, left atrium and the airway of 10.5 and 5 cmH2O, respectively. Blood PO2, PCO2 and pH are held at respectively, 140 torr, 35 torr and 7.4 (NPT7, Radiometer). A heat exchanger maintains perfusate temperature at 37° C. (Yellow Springs, 44TD).

E. Lung Positioning for Microscopy.

Lungs are positioned on a vibration free air table (Micro-G, Technical Manufacturing Corp.). Imaging is carried out by means of wide-angle (WAM), confocal (LSM) or two-photon (2P) microscopy. The lung is placed under the objective of an upright microscope (WAM: Olympus AX-70; LSM: Zeiss LSM 510 META; 2P: Radiance 2100, Nikon Eclipse E600 FN). For WAM, excitation light (Mercury lamp) is passed through a filter wheel (Lambda-10, Sutter Inst.) and dichroic mirrors equipped with appropriate filters. WAM images are acquired by imaging software (Universal Imaging) through UV c compatible objectives (40× Fluor LWD, Nikon), dichroic mirrors and emission filters (400 DCLPO2; 510WB40, Omega Optical) and a 16-bit digital camera (Roper CCD72, Photometrics CoolSnap HQ). Background is determined from images captured prior to dye loading.

Arterial and venular capillaries (diameter 15-25 μm) are identified by their divergent and convergent flows, respectively. Septal capillaries have smaller diameter (<10 μm). To induce fluorescence in EC in situ, capillaries are infused with fluorophores. For example, for ROS (reactive oxygen species) detection, we infuse membrane-permeable DCFH-DA that intracellularly converts to DCFH. ROS oxidizes DCF to fluorescent DCF.

F. ALI Protocols.

To establish the ALI models described above rats or mice are anesthetized using ketamine-xylazine. Then intra-tracheal instillations of HCl (2 ml/kg, 0.1N, pH 1.5), lipopolysaccharide (E. coli derived, 1 mg/kg), or bleomycin (3 mg/kg) are done. The animals are then allowed to recover.

EVLW is determined by the blood-free wet-dry method. Kfc is determined by weighing lungs on a force transducer (Gould). Both methods are well-established in our laboratory (5, 6, 67).

G. GFP-FRNK Transfection.

The plasmid DNA is a gift (Dr. Parsons, University of Virginia, Charlottesville, Va.). We transformed the DNA in competent bacteria (DH5-α, Invitrogen) and amplified kanamycin resistant colonies (Maxiprep, Qiagen). The cDNA construct encoding the amino-terminal green fluorescent protein (GFP)-tagged variant of FRNK was generated by cloning chicken FRNK into the BglII/EcoRI sites of the mammalian expression vector pEGFP-C1. Digestion with restriction enzyme, HindIII, give 2 fragments, 870 by and 4.9 kb conformed the GFP-FRNK plasmid. WHAT DID YOU USE GFP-FRNK FOR?

H. In Situ Immunoimaging.

These methods are established (5,41)). By microinfusion, capillaries are permeabilized with 0.01% saponin ×1 min, then fixed with a 50:50 mixture of acetone and methanol, blocked with 20% horse serum, and injected with specific primary mAb, followed by FITC-labeled, secondary IgG targeted specifically to the primary, and then a buffer wash. Control data is obtained using isotype-matched, non-specific primary Ab, and fluorescent secondary alone. The cells are imaged using confocal or two-photon microscopy.

I. Split-drop Technique.

In the isolated, perfused lung (5,57-62), an oil drop is microinjected into a microvessel and then split with a test solution (vehicle: isosmolar Ringer's buffer containing 4% albumin). As the test solution filters across the capillary wall, the distance (split length) between the two segments of the split oil drop, hence the split-drop volume (V), progressively decreases. From analyses of video-recorded data, split-drop volume is plotted against time and filtration rate (Jv) is calculated in terms of the surface area of filtration. The slope of the line relating Jv to capillary pressure (Pc) at two levels of Pc gives the hydraulic conductivity, Lp. The split-drop procedure takes ~2 minutes.

J. FAKp Infusion in Chariot©.

Chariot© reagent (1 μL) is prepared in a DMSO-Pluronic (20%) mixture (10 μL), and BODIPY-FAKp (10 μL) in HEPES buffer containing 4% dextran. The solutions are then mixed with gentle agitation at room temperature for 30 minutes. Then, Hepes-dextran buffer is added to make a final volume (600 μL). FAKp is bound to Chariot© reagent to make a Chariot©-FAKp product. Concentrations in the final injected solution are 5-25 ug/ml FAKp in Chariot© reagent. For isolated lung experiments, the solution was given either by infusion to a localized microvascular region through a wedged venous catheter introduced through the left atrium as we have previously reported (41,42), or added directly to the lung perfusion. For intact lung experiments, the solution is injected in the tail vein.

K. RT-PCR Primers.

RT-PCR of E-cadherin used the primers described in the provisional application U.S. 60/976,779, filed Oct. 1, 2007, incorporated herein by reference.

In the foregoing specification, the invention has been described with reference to specific embodiments. It will, however, be evident that various modifications and changes may be made without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

BIBLIOGRAPHY

1. Quadri, S., M., K. Parthasarathi, T. Tanita and J. Bhattacharya. Endothelial barrier strengthening by activation of focal adhesion kinase. J. Biol. Chem. 2003. 278:13342-9.

2. Rubenfeld G D, Caldwell E, Peabody E, Weaver J, Martin D P, Neff M, Stern E J, Hudson L D. Incidence and outcomes of acute lung injury. N Engl J. Med. 2005; 353: 1685-93.

3. Mehta D, Malik A B. Signaling mechanisms regulating endothelial permeability. Physiol Rev. 2006; 86:279-367.

4. Bhattacharya, S., Quadri, S., and J. Bhattacharya. Endothelial-Matrix Interactions in the Lung. In: Advances in Molecular and Cellular Biology. Vol. 36, Perspectives on Lung Endothelial Barrier Function Editor: C. E. Patterson. Elsevier, Amsterdam. 2004.

5. Safdar, Z, P. Wang, H. Ichimura, A. C. Issekutz, S. Quadri and J. Bhattacharya. Hyperosmolarity enhances the lung capillary barrier. J. Clin. Invest. 2003. 112:1541-9.

6. Safdar, Z, G. Grunig, and J. Bhattacharya Inhibition of acid-induced lung injury by hyperosmolar sucrose in rats. Am. J. Resp. Crit. Care Med. 2005. 172:1002-1007.

7. Garcia J G, Liu F, Verin A D, Birukova A, Dechert M A, Gerthoffer W T, Bamberg J R, English D. Sphingosine 1-phosphate promotes endothelial cell barrier integrity by Edg-dependent cytoskeletalrearrangement. J Clin Invest. 2001; 108:689-701.

8. McVerry B J, Peng X, Hassoun P M, Sammani S, Simon B A, Garcia J G. Sphingosine 1-phosphate reduces vascular leak in murine and canine models of acute lung injury. Am J Respir Crit. Care Med. 2004; 170:987-93.

9. Cullere X, Shaw S K, Andersson L, Hirahashi J, Luscinskas F W, and Mayadas T N. Regulation of vascular endothelial barrier function by Epac, a cAMP-activated exchange factor for Rap GTPase. Blood 105: 1950-1955, 2005.

10. Wittchen E S, van Buul J D, Burridge K, and Worthylake R A. Trading spaces: Rap, Rac, and Rho as architects of transendothelial migration. Curr Opin Hematol 12: 14-21, 2005.

11. Serikov V B, Glazanova T V, Jerome E H, Fleming N R, Higashimori H, Staub N C Sr. Tyloxapol attenuates the pathologic effects of endotoxin in rabbits and mortality following cecal ligation and puncture in rats by blockade of endotoxin receptor-ligand interactions. Inflammation. 2003; 27:175-90.

12. Mitra S K, Schlaepfer D D. Integrin-regulated FAK-Src signaling in normal and cancer cells. Curr Opin Cell Biol. 2006; 18:516-23.

13. Holinstat M, Knezevic N, Broman M, Samarel A M, Malik A B, Mehta D. Suppression of RhoA activity by focal adhesion kinase-induced activation of p190RhoGAP: role in regulation of endothelial permeability. J Biol. Chem. 2006; 281:2296-305.

14. Mehta D, Tiruppathi C, Sandoval R, Minshall R D, Holinstat M, and Malik A B. Modulatory role of focal adhesion kinase in regulating human pulmonary arterial endothelial barrier function. J Physiol 2002; 539:779-789.

15. Wu M H, Guo M, Yuan S Y, Granger H J. Focal adhesion kinase mediates porcine venular hyperpermeability elicited by vascular endothelial growth factor. J. Physiol. 2003; 552: 691-9.

16. Usatyuk P V, Natarajan V. of reactive oxygen species-induced endothelial cell-cell and cell-matrix contacts by focal adhesion kinase and adherens junction proteins. Am J Physiol Lung Cell Mol. Physiol. 2005; 289:L999-1010.

17. Parker J C, Stevens T, Randall J, Weber D S, King J A. Hydraulic conductance of pulmonary microvascular and macrovascular endothelial cell monolayers. Am J Physiol Lung Cell Mol. Physiol. 2006; 291:L30-7.

18. Kornberg L, Earp H S, Parsons J T, Schaller M, and Juliano R L. Cell adhesion or integrin clustering increases phosphorylation of a focal adhesion-associated tyrosine kinase. J Biol Chem 267: 23439-23442, 1992.

19. Quadri, S, and J. Bhattacharya. Resealing of endothelial junctions by focal adhesion kinase. Am J Physiol Lung Cell Mol. Physiol. 2007; 292:L334-42.

20. Lampugnani M G, Zanetti A, Breviario F, Balconi G, Orsenigo F, Corada M, Spagnuolo R, Betson M, Braga V, 20. Dejana E. VE-cadherin regulates endothelial actin activating Rac and increasing membrane association of Tiam. Mol Biol Cell. 2002; 13:1175-89.

21. Knudsen K A, Soler A P, Johnson K R, Wheelock M J. Interaction of alpha-actinin with the cadherin/catenin cell-cell adhesion complex via alpha-catenin. J. Cell Biol. 1995; 130:67

22. Izaguirre G, Aguirre L, Hu Y P, Lee H Y, Schlaepfer D D, Aneskievich B J, Haimovich B. The cytoskeletal/non-muscle isoform of alpha-actinin is phosphorylated on its actin-binding domain by the focal adhesion kinase. J Biol. Chem. 2001; 276:28676-85.

23. Izard T, Evans G, Borgon R A, Rush C L, Bricogne G, Bois P R. Vinculin activation by talin through helical bundle conversion. Nature. 2004; 427:171-5.

24. Bois P R, O'Hara B P, Nietlispach D, Kirkpatrick J, Izard T. The vinculin binding sites of talin and alphaactinin are sufficient to activate vinculin. J Biol. Chem. 2006; 281: 7228-36.

25. Godzich M, Hodnett M, Frank J A, Su G, Pespeni M, Angel A, Howard M B, Matthay M A, Pittet J F. Activation of the stress protein response prevents the development of pulmonary edema by inhibiting VEGF cell signaling in a model of lung ischemia-reperfusion injury in rats. FASEB J. 2006 July; 20(9):1519-21.

26. Subauste M C, Nalbant P, Adamson E D, Hahn K M. Vinculin controls PTEN protein level by maintaining the interaction of the adherens junction protein beta-catenin with the scaffolding protein MAGI-2. J Biol. Chem. 2005 Feb. 18; 280(7):5676-81.

27. Fukata M, Kuroda S, Nakagawa M, Kawajiri A, Itoh N, Shoji I, Matsuura Y, Yonehara S, Fujisawa H, Kikuchi A, Kaibuchi K. Related Articles, Cdc42 and Rac1 regulate the interaction of IQGAP1 with betacatenin. J Biol. Chem. 1999; 274(37):26044-50.

28. Stockton R A, Schaefer E, Schwartz M A. p21-activated kinase regulates endothelial permeability through modulation of contractility. J Biol. Chem. 2004 Nov. 5; 279 (45):46621-30.

29. Dan C, Kelly A, Bernard O, Minden A. Related Articles, Cytoskeletal changes regulated by the PAK-4 serine/threonine kinase are mediated by LIM kinase 1 and cofilin. J Biol. Chem. 2001 Aug. 24; 276(34):32115-21.

30. Turner C E. Related Articles, Paxillin interactions. J Cell Sci. 2000; 113:4139-40.

31. Kiyokawa E, Hashimoto Y, Kobayashi S, Sugimura H, Kurata T, Matsuda M. Related Articles, Activation of Rac1 by a Crk SH3-binding protein, DOCK180. Genes Dev. 1998 Nov. 1; 12(21):3331-6.

32. Grimsley C M, Kinchen J M, Tosello-Trampont A C, Brugnera E, Haney L B, Lu M, Chen Q, Klingele D, Hengartner M O, Ravichandran K S. Related Articles, Dock180 and ELMO1 proteins cooperate to promote evolutionarily conserved Rac-dependent cell migration. J Biol. Chem. 2004 Feb. 13; 279(7):6087-97. Epub 2003 Nov. 24.

33. Lu M, Kinchen J M, Rossman K L, Grimsley C, Hall M, Sondek J, Hengartner M O, Yajnik V, Ravichandran K S. Related Articles, A Steric-inhibition model for regulation of nucleotide exchange via the Dock180 family of GEFs. Curr Biol. 2005 Feb. 22; 15(4):371-7.

34. Valles A M, Beuvin M, Boyer B. Activation of Rac1 by paxillin-Crk-Dock 180 signaling complex is antagonized by Rap1 in migrating NBT-II cells. J. Biol. Chem. 2004 Oct. 22; 279(43):44490-6.

35. Withers B E, Keller P R, Fry D W. Related Articles, Expression, purification and characterization of focal adhesion kinase using a baculovirus system. Protein Expr Purif. 1996 February; 7(1):12-8.

36. Nobes C D, Hall A. Rho, rac, and cdc42 GTPases regulate the assembly of multimolecular focal complexes associated with actin stress fibers, lamellipodia, and filopodia. Cell. 1995 Apr. 7; 81(1):53-62.

37. Palovuori R, Eskelinen S. Role of vinculin in the maintenance of cell-cell contacts in kidney epithelial MDBK cells. Eur J. Cell Biol. 2000 December; 79(12):961-74.

38. Morris M C, Depollier J, Mery J, Heitz F, and Divita G. A peptide carrier for the delivery of biologically active proteins into mammalian cells. Nat Biotechnol 19: 1173-1176, 2001.

39. Aoshiba K, Yokohori N, and Nagai A. Alveolar wall apoptosis causes lung destruction and emphysematous changes. Am J Respir Cell Mol Biol 28: 555-562, 2003.

40. Maron M B, Folkesson H G, Stader S M, Walro J M. PKA delivery to the distal lung air spaces increases alveolar liquid clearance after isoproterenol-induced alveolar epithelial PKA desensitization. Am J Physiol Lung Cell Mol. Physiol. 2005 August; 289(2):L349-54.

41. Kuebler, W. M., K. Parthasarathi, P. M. Wang, and J. Bhattacharya. A novel signaling mechanism between gas and blood compartments of the lung. J. Clin. Invest. 2000; 105 905-913.

42. Ichimura, H., K. Parthasarathi, S. Quadri, A. C. Issekutz and J. Bhattacharya. Mechano-oxidative coupling by mitochondria induces P-selectin expression in lung capillaries. J. Clin. Invest. 2003. 111:691-699.

43. Kuebler, W. M., K. Parthasarathi, J. Lindert and Bhattacharya, J. Real-time lung microscopy. J. Appl. Physiol. (in press).

44. Martin K H, Boerner S A, Parsons J T. Regulation of focal adhesion targeting and inhibitory functions of the FAK related protein FRNK using a novel estrogen receptor "switch". Cell Motil Cytoskeleton. 2002 February; 51(2):76-88.

45. Pirone D M, Liu W F, Ruiz S A, Gao L, Raghavan S, Lemmon C A, Romer L H, Chen C S. An inhibitory role for FAK in regulating proliferation: a link between limited adhesion and RhoA-ROCK signaling. J. Cell Biol. 2006 Jul. 17; 174(2):277-88.

46. Joanna M. Watson, Timothy W. Harding, Vita Golubovskaya. Inhibition of the calcium-dependent tyrosine kinase (CADTK) blocks monocyte spreading and motility. J Biol. Chem. 276: 3536-3542, 2001.

47. Kirchner J, Kam Z, Tzur G, Bershadsky A D, Geiger B. Live-cell monitoring of tyrosine phosphorylation in focal adhesions following microtubule disruption. J Cell Sci. 2003 Mar. 15; 116(Pt 6):975-86.

48. Bhattacharya, S., N. Sen, M. Yiming, R. Patel, K. Parthasarathy, S. Quadri, A. Issekutz and J. Bhattacharya. High tidal volume ventilation induces proinflammatory signaling in rat lung endothelium. Am J Respir Cell Mol. Biol. 2003 February; 28(2):218-24.

49. Zemljic-Harpf A E, Ponrartana S, Avalos R T, Jordan M C, Roos K P, Dalton N D, Phan V Q, Adamson E D, Ross R S. Heterozygous inactivation of the vinculin gene predisposes to stress-induced cardiomyopathy. Am J. Pathol. 2004 September; 165(3):1033-44.

50. Kiyokawa E, Hashimoto Y, Kurata T, Sugimura H, Matsuda M. Related Articles, Evidence that DOCK180 up-regulates signals from the CrkII-p130(Cas) complex. J Biol. Chem. 1998 Sep. 18; 273(38):24479-84.

51. Le T L, Yap A S, Stow J L. Recycling of E-cadherin: a potential mechanism for regulating cadherin dynamics. J. Cell Biol. 1999 Jul. 12; 146(1):219-32.

52. Le T L, Joseph S R, Yap A S, Stow J L. Protein kinase C regulates endocytosis and recycling of E-cadherin. Am J Physiol Cell Physiol. 2002; 283:C489-99.

53. Turner C E, Glenney J R Jr, Burridge K. Paxillin: a new vinculin-binding protein present in focal adhesions. J. Cell Biol. 1990; 111:1059-68.

54. Wood C K, Turner C E, Jackson P, Critchley D R. Characterisation of the paxillin-binding site and the Cterminal focal adhesion targeting sequence in vinculin. J Cell Sci. 1994; 107:709-17.

55. King J, Hamil T, Creighton J, Wu S, Bhat P, McDonald F, Stevens T. Structural and functional characteristics of lung macro- and microvascular endothelial cell phenotypes. Microvasc Res. 2004; 67:139-51.

56. Parker J C, Yoshikawa S. Vascular segmental permeabilities at high peak inflation pressure in isolated rat lungs. Am J Physiol Lung Cell Mol. Physiol. 2002; 283:L1203-9.

57. Bhattacharya, J. Hydraulic conductivity of lung venules determined by split-drop technique. J. Appl. Physiol. 64:2565-2567, 1988.

58. Qiao, Ren-Li and J. Bhattacharya. Segmental barrier properties of the pulmonary microvascular bed. J. Appl. Physiol 71:2152-2159, 1991.

59. Ishikawa, S., H. Tsukada and J. Bhattacharya. Soluble complex of complement increases hydraulic conductivity in single microvessels of rat lung. J. Clin. Invest. 91:103-109, 1993.

60. Qiao, Ren-Li, R. Sadurski and J. Bhattacharya. Hydraulic conductivity of ischemic pulmonary venules. Am. J. Physiol.: Lung Cell. Mol. Physiol. 264:382-386, 1993.

61. Qiao, Ren-Li, X. Ying and J. Bhattacharya. Hyperoncotic albumin decreases the endothelial barrier in rat lung. Am. J. Physiol. 265:H198-H204, 1993.

62. Tsukada, H., X. Ying, C. Fu, S. Ishikawa, P. McKeown-Longo, S. Albelda, S. Bhattacharya, B. A. Bray and J. Bhattacharya. Ligation of endothelial_v_3 integrin increases capillary hydraulic conductivity of rat lung. Circ. Res. 77:651-659, 1995.

63. Goldmann W H, Galneder R, Ludwig M, Xu W, Adamson E D, Wang N, Ezzell R M. Differences in elasticity of vinculin-deficient F9 cells measured by magnetometry and atomic force microscopy. Exp Cell Res. 1998; 239:235-42.

64. Goldmann W H. The coupling of vinculin to the cytoskeleton is not essential for mechano-chemical signaling in F9 cells. Cell Biol Int. 2002; 26:279-86.

65. Bhattacharya, S., C. Fu, J. Bhattacharya and S. Greenberg. Soluble ligands of the_v_3 integrin mediate enhanced tyrosine phosphorylation of multiple proteins in adherent bovine pulmonary artery endothelial cells. J. Biol. Chem. 270:16781-16787, 1995.

66. Bhattacharya, S., X. Ying, C. Z. Fu, R. Patel, W. Kuebler, S. Greenberg and J. Bhattacharya. The αvβ3 integrin induces tyrosine phosphorylation-dependent [Ca2+]i influx in pulmonary endothelial cells. Circ Res. 86:456-462, 2000.

67. Parthasarathi K, Ichimura H, Monma E, Lindert J, Quadri S, Issekutz A, Bhattacharya J. Connexin 43 mediates spread of Ca2+-dependent proinflammatory responses in lung capillaries. Clin Invest. 2006; 116:2193-200.

68. Yano H, Mazaki Y, Kurokawa K, Hanks S K, Matsuda M, Sabe H. Roles played by a subset of integrin signaling molecules in cadherin-based cell-cell adhesion. J. Cell Biol. 2004; 166:283-95.

69. Su G, Hodnett M, Wu N, Atakilit A, Kosinski C, Godzich M, Huang X Z, Kim J K, Frank J A, Matthay M A, Sheppard D, Pittet J F. Integrin alphavbeta5 regulates lung vascular permeability and pulmonary endothelial barrier function. Am J Respir Cell Mol. Biol. 2007; 36:377-86.

70. Schober M, Raghavan S, Nikolova M, Polak L, Pasolli H A, Beggs H E, Reichardt L F, Fuchs E. Focal adhesion kinase modulates tension signaling to control actin and focal adhesion dynamics. J. Cell Biol. 2007; 176:667-80.

71. Bhattacharya J. Interpreting the lung microvascular filtration coefficient. Am J Physiol Lung Cell Mol. Physiol. 2007 Apr. 27; [Epub ahead of print]

72. Huang X. and Miller W. Adv. Appl. Math. 1991. A time-efficient, linear-space local similarity Algorithm. 12:373-381.

73. Medley Q G, Buchbinder E G, Tachibana K, Ngo H, Serra-Pagès C, Streuli M. Signaling between focal adhesion kinase and trio. J Biol. Chem. 2003; 278:13265-70.

74. Schwarze S R, Vocero-Akbani A Ho, Dowdy S F. In vivo protein transduction: delivery of a biologically active protein into the mouse. Science. 1999; 285:1569-1572.

75. Asoh S, Ohsawa I, Mori T, et al. Protection against ischemic brain injury by protein therapeutics. Proc Natl Acad Sci USA. 2002; 99:17107-17112.

76. Cao G, Pei W, Ge H. In vivo delivery of a Bcl-$x_L$ fusion protein containing the TAT protein transduction domain protects against ischemic brain injury and neuronal apoptosis. J. Neurosci. 2002; 22:5423-5431.

77. Denicourt C, Dowdy S F. Protein transduction technology offers novel therapeutic approach for brain ischemia. Trends Pharmacol Sci. 2003; 24:216-218.

78. Sugioka R, Shimizu S, Funatsu T, Tamagawa H, Sawa Y, Kawakami T, Tsujimoto Y. BH4-domain peptide from Bcl-xL exerts anti-apoptotic activity in vivo. Oncogene. 2003; 22:8432-8440.

79. Zhou Y, Du W, Koretsky T, Bagby G C, Pang Q. TAT-mediated intracellular delivery of NPM-derived peptide induces apoptosis in leukemic cells and suppresses leukemogenesis in mice. Blood. 2008 Sep. 15; 112(6):2474-83.

80. Gustafsson A B, Gottlieb R A, Granville D J. TAT-mediated protein transduction:
delivering biologically active Mol Med 2005:112:81-90.

What is claimed is:

1. A method for treating or preventing acute lung injury and acute respiratory distress syndrome in an animal, comprising administering a therapeutically effective amount of activated phosphorylated focal adhesion kinase wherein the tyrosine at position 397 is phosphorylated or a biologically active fragment, derivative or variant thereof.

2. The method of claim 1, wherein the activated focal adhesion kinase is human activated phosphorylated focal adhesion kinase.

3. The method of claim 2, wherein the human activated phosphorylated focal adhesion kinase is a recombinant protein.

4. The method of claim 1, further comprising administering a therapeutically effective amount of high osmolar sucrose.

5. The method of claim 4, wherein the activated phosphorylated focal adhesion kinase and high osmolar sucrose are administered on the same day.

6. The method of claim 1, wherein the activated phosphorylated focal adhesion kinase is administered intravenously or by inhalation.

7. The method as in claim 1, wherein the therapeutically effective amount of activated phosphorylated focal adhesion kinase is an amount of from about 0.1-20 micrograms/kilogram body weight.

8. The method of claim 1, wherein the activated focal adhesion kinase is bound to a transport protein that is a member selected from the group comprising Chariot™, pepetratin, TAT fragment, a signal sequence-based peptide, and transportan.

* * * * *

SEQUENCE LISTING

```
<160> NUMBER OF SEQ ID NOS: 6

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide
```

```
<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide

<400> SEQUENCE: 2

Gly Arg Lys Lys Arg Arg Gln Arg Arg Pro Pro Gln
1               5                   10

<210> SEQ ID NO 3
<211> LENGTH: 27
<212> TYPE: PRT
<213> ORGANISM: Artificial Sequence
<220> FEATURE:
<223> OTHER INFORMATION: Synthetic peptide

<400> SEQUENCE: 3

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

Ala Ala Val Ala Leu Leu Pro Ala Val Leu Leu Ala Leu Leu Ala Pro
1               5                   10                  15

<210> SEQ ID NO 5
<211> LENGTH: 26
<212> TYPE: PRT
<213> ORGANISM: Artificial Sequence
<220> FEATURE:
<223> OTHER INFORMATION: Synthetic peptide

<400> SEQUENCE: 5

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 6
<211> LENGTH: 18
<212> TYPE: PRT
<213> ORGANISM: Artificial Sequence
<220> FEATURE:
<223> OTHER INFORMATION: Synthetic peptide

<400> SEQUENCE: 6

Lys Leu Ala Leu Lys Leu Ala Leu Lys Ala Leu Lys Ala Ala Leu Lys
1               5                   10                  15

Leu Ala
```